United States Patent
Tripier et al.

(10) Patent No.: US 10,434,199 B2
(45) Date of Patent: Oct. 8, 2019

(54) PICOLINATE CROSS-BRIDGED CYCLAMS, CHELATES WITH METALLIC CATIONS AND USE THEREOF

(71) Applicants: UNIVERSITÉ DE BRETAGNE OCCIDENTALE, Brest (FR); CENTRE NATIONAL DE LA RECHERCHE SCIENTIFIQUE (CNRS), Paris (FR)

(72) Inventors: Raphael Tripier, Kersaint-Plabennec (FR); Zakaria Halime, Brest (FR)

(73) Assignees: UNIVERSITÉ DE BRETAGNE OCCIDENTALE, Brest (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 494 days.

(21) Appl. No.: 15/036,133

(22) PCT Filed: Nov. 12, 2014

(86) PCT No.: PCT/EP2014/074415
§ 371 (c)(1),
(2) Date: May 12, 2016

(87) PCT Pub. No.: WO2015/071334
PCT Pub. Date: May 21, 2015

(65) Prior Publication Data
US 2016/0287733 A1   Oct. 6, 2016

(30) Foreign Application Priority Data
Nov. 12, 2013 (EP) .................................... 13192597

(51) Int. Cl.
| | |
|---|---|
| *A61K 51/00* | (2006.01) |
| *A61M 36/14* | (2006.01) |
| *A61K 51/10* | (2006.01) |
| *C07D 487/08* | (2006.01) |
| *A61K 51/04* | (2006.01) |
| *C07B 59/00* | (2006.01) |
| *C07K 16/32* | (2006.01) |
| *A61K 47/68* | (2017.01) |
| *A61K 49/04* | (2006.01) |

(52) U.S. Cl.
CPC ...... *A61K 51/1075* (2013.01); *A61K 47/6803* (2017.08); *A61K 47/6871* (2017.08); *A61K 51/0482* (2013.01); *A61K 51/1093* (2013.01); *C07B 59/002* (2013.01); *C07D 487/08* (2013.01); *C07K 16/32* (2013.01); *A61K 49/04* (2013.01); *C07B 2200/05* (2013.01); *C07K 2317/24* (2013.01)

(58) Field of Classification Search
None
See application file for complete search history.

(56) References Cited

U.S. PATENT DOCUMENTS 9,061,078 B2 * 6/2015 Yoo .................... A61K 51/0482

FOREIGN PATENT DOCUMENTS

| JP | 2001-316253 | 11/2011 |
|---|---|---|
| WO | 2011/031073 | 3/2011 |
| WO | 2012/037648 | 3/2012 |
| WO | 2013/072491 | 5/2013 |

OTHER PUBLICATIONS

Hubin (Coord. Chem. Reviews 2003, 241, 27-46).*
Anderson et al., "Copper-64 radiopharmaceuticals for PET imaging of cancer: advances in preclinical and clinical research", Cancer Biotherapy and Radiopharmaceuticals, vol. 24, No. 4, 2009, pp. 379-393.
Bailey et al., "H2azapa: a versatile acyclic multifunctional chelator for 67Ga, 64Cu, 111In, and 177Lu", Inorganic chemistry, vol. 51, 2012, pp. 12575-12589.
Boros et al., "Acyclic chelate with ideal properties for 68Ga PET imaigng agent elaboration", JACS, vol. 132, 2010, pp. 15726-15733.
Boros et al., "New Ga derivatives of the H2dedpa scaffold with improved clearance and persistent heart uptake", Nuclear Medicine and Biology, vol. 38, No. 8, 2011, pp. 1165-1174.
Boros et al., "Evaluation of the H2dedpa scaffold and its cRGDyK conjugates for labeling with 64Cu", Inorganic Chemistry, vol. 51, 2012, pp. 6279-6284.
Boros et al., "RGD conjugates of the H2dedpa scaffold: synthis, labeling and imaging with 68Ga", Nuclear Medicine and Biology, vol. 39, No. 6, 2012, pp. 785-794.
Chaves et al., "The stability of the metal complexes of cyclic tetra-aza tetra-acetic acids", Talanta, vol. 39, No. 3, 1992, pp. 249-254.
Delgado et al., "Metal complexes of cyclic tetra-azatetra-acetic acids", Talanta, vol. 29, 1982, pp. 815-822.

(Continued)

*Primary Examiner* — Michael G. Hartley
*Assistant Examiner* — Melissa J Perreira
(74) *Attorney, Agent, or Firm* — Young & Thompson

(57) ABSTRACT

Chelates resulting from the complexation of picolinate cross-bridged cyclams of formula (I), wherein n and the substituents L1-L4 and R1-R5 are as defined, with metallic cations. Picolinate cross-bridged cyclam ligands of formula (I), the use of chelates in nuclear medicine and the use of ligands in cations detection or epuration of effluents are also described.

13 Claims, 1 Drawing Sheet

(56) References Cited

OTHER PUBLICATIONS

Lima et al., "Monopicolinate cyclen and cylam derivatives for stable copper(II) complexation", Inorganic Chemistry, vol. 51, No. 12, 2012, pp. 6916-6927.
Mato-Iglesias et al., "Lanthanide complexes based on a 1,7-diaza-12-crown-4 platform containing picolinate pendants: a new structural entry for the design of magnetic resonance imaging contrast agents", Inorganic Chemistry, vol. 47, 2008, pp. 7840-7851.
Rodriguez-Rodriguez et al., "Lanthanide (III) complexes with ligands derived from a cyclen framework containing pyridincarboxylate pendants. The effect of steric hindrance on the hydration number", Inorganic Chemistry, vol. 51, 2012, pp. 2509-2521.
Rodriguez-Rodriguez et al., "Solution structure of Ln(III) complexes with macrocyclic ligands through theoretical evaluation of 1H NMR contact shifts", Inorganic Chemistry, vol. 51, 2012, pp. 13419-13429.
Roger et al., "Monopicolinate-dipicolyl derivative of triazacyclononane for stable complexation of Cu2+ and 64Cu2+", Inorganic Chemistry, vol. 21, No. 9, 2013, pp. 5246-5259.
Silversides et al. "Challenges in chelating positron emitting copper isotopes: tailored synthesis of unsymmetric chelators to form ultra stable complexes", Danton Transactions, vol. 40, No. 23, 2011, pp. 6289-6297.
Sun et al., "Radiolabeling and in vivo behavior of copper-64-labeled cross-bridged cyclam ligands", Journal of Medicinal Chemistry, vol. 45, No. 2, 2002, pp. 469-477.
Wong et al., "Synthesis and characterization of cross-bridged cyclam and pendant-armed derivatives and structural studies of their copper(II) complexes", JACS, vol. 122, 2000, pp. 10561-10572.
Lebedev, A. Y. et al., "Clickable bifunctional radiometal chelates for peptide labeling," Chemical Communications, 2010, vol. 46., No. 10., pp. 1706-1708.
Zeng, D. et al., "New cross-bridged cyclam derivative Cb-TE1K1P, an improved bifunctional chelator for copper radionuclides," Chemical Communications, 2014, vol. 50, No. 1, pp. 43-45.

* cited by examiner

PICOLINATE CROSS-BRIDGED CYCLAMS, CHELATES WITH METALLIC CATIONS AND USE THEREOF

FIELD OF INVENTION

The present invention relates to chelates resulting from the complexation of picolinate cross-bridged cyclams with metallic cations, preferably copper (II) or gallium (III). The invention further relates to picolinate cross-bridged cyclam ligands. Another object of the invention is the use of chelates of the invention in nuclear medicine and the use of ligands of the invention in cations detection or epuration of effluents.

BACKGROUND OF INVENTION

Tetraazamacrocycles such as derivatives of cyclam (1,4,8,11-tetraazacyclotetradecane) generate an important interest in many fields such as medicine, especially nuclear medicine; epuration of effluents contaminated with radioactive elements or metals such as lead; catalysis; solid/liquid extraction and liquid/liquid extraction; or detection of traces of metallic cations. The present invention relates to all these fields of applications, especially nuclear medicine.

In nuclear medicine, radiopharmaceuticals used as therapeutic agents or as imaging agents often comprise chelates of radioelements. To improve the efficiency of radiopharmaceuticals, a targeting biomolecule may be appended on the chelating moiety in order to induce a site-specific delivery of the radiation, leading to a bifunctional chelating agent (BCA). Obtaining a BCA requires the introduction of an appropriate conjugation group in the structure of the metal chelator, to allow for the bioconjugation prior or after labeling with the radioisotope. The targeting agent may be for example an antibody, an hapten or a peptide. Depending on the nature of the radionuclide, it is for example possible to perform PET imaging (Positron Emission Tomography), SPECT (Single Photon Emission Computed Tomography) or RIT (RadioImmunoTherapy).

For applications in nuclear medicine, the chelate should thus be bioconjugated to a biological vector while trapping the radionuclide to form a stable complex preventing the release of the metal in the organism. Moreover, when using radioactive emitters, the kinetic constraint has to be considered because of the limited half-life of the radionuclide.

Dota (1,4,7,10-tetraazacyclododecane-1,4,7,10-tetraacetic acid) is a tetra N-functionalized cyclen (scheme 1). In scheme 1, dota is referred to as "$H_4$dota", the four hydrogen atoms specified before "dota" reflecting the fact that in order to have the four carboxylic acid functions in "COOH" form, the four amines of the macrocycle should be protonated. The same nomenclature is used along the description for macrocycles comprising carboxylic acid functions.

Dota is the most used ligand to complex gadolinium (III) for MRI imaging. Dota also enables to complex other metals commonly used in nuclear medicine, such as for example $^{111}$In, $^{68}$Ga, $^{149}$Tb, $^{213}$Bi, $^{212}$Bi, $^{212}$Pb, $^{64}$Cu or $^{67}$Cu. Derivatives of the dota, are today widely studied (scheme 1).

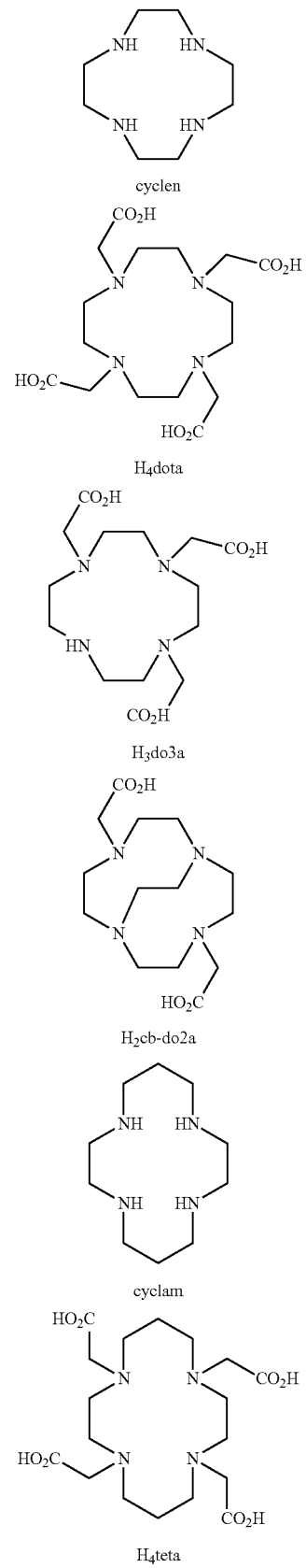

Scheme 1. Cyclen and cyclam derivatives.

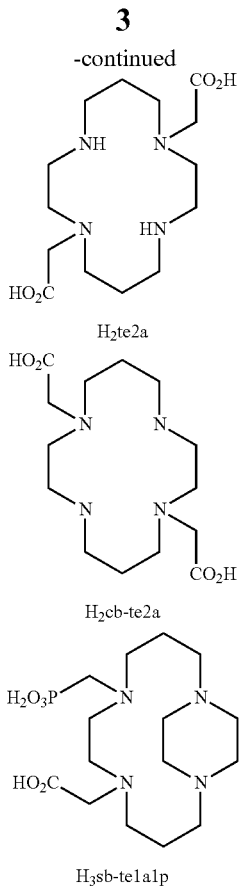

H₂te2a

H₂cb-te2a

H₃sb-te1a1p

Among the range of potentially useful metals in nuclear medicine, copper has been receiving much interest due to the existence of several radionuclides with different half-life times and emission properties suitable for diagnostic imaging or therapeutic applications. The most interesting nuclides are $^{67}$Cu ($t_{1/2}$=62.0 h, β⁻ 100%, $E_{max}$=0.577 MeV) for radiotherapy, and $^{64}$Cu ($t_{1/2}$=12.7 h, β⁺17.4%, $E_{max}$=0.656 MeV, β⁻ 39.6%, $E_{max}$=0.573 MeV) for both positron emission tomography (PET) and radiotherapy. Copper exists predominantly as divalent metal cation that prefers donor groups such as amines and anionic carboxylates to form complexes with coordination numbers of 4-6. High coordination numbers are usually preferred, often providing square pyramidal, trigonal bipyramidal or octahedral geometries, so as to entirely surround the metal cation. Within the vast range of acyclic and cyclic ligands successfully used for copper complexation, the family of tetraaza macrocycles with N-appended coordinating arms stands out owing to the efficiency and versatility of its copper chelation.

Like copper, gallium prefers high coordination numbers, especially under the form of octahedral geometries and tetraaza macrocycles with N-appended coordinating arms may be used for its chelation. The most interesting nuclide for nuclear imaging is $^{68}$Ga ($t_{1/2}$=68 min, β⁺100%, $E_{max}$=2.921 MeV), for positron emission tomography (PET).

The following requirements are commonly admitted in the art as specifications for an optimized chelate intended to be used in nuclear medicine:
a) rapid metallation kinetics with respect to the time of the radionuclide half-life, even under the acidic conditions in which most radionuclides are produced;
b) a very good thermodynamic stability;
c) inertness with respect to other metals, especially $Zn^{2+}$ which is present in high amounts in the biological medium or as byproduct of radionuclides production such as $^{64}$Cu;
d) kinetic inertness;
e) stability upon reduction in the biological media of the chelated metal, such as for example the stability of copper (I) complex as a reduced form of the initially chelated copper (II).

Metallation kinetics (point a) may be determined using UV-visible spectrometry by measuring the increasing intensity of the complex d-d transition band. When possible, i.e. depending on whether the metal is paramagnetic or not, metallation kinetics may also be determined by NMR. Suitable metallation kinetics depends on the half-life of the radionuclide used to form the chelate.

Thermodynamic stability (point b) may be evaluated by determining the stability constants of the complexes, especially the association constant K and pK (or log K).

Stability constants may be measured by potentiometry or spectroscopies. pM values may be calculated from pK in order to compare thermodynamic stability with corresponding values of other ligands of the prior art. Indeed, pM reflects the amount of ligand not chelated, taking into account the basicity of the ligand. In the present invention, a "very good thermodynamic stability" refers to a thermodynamic stability at least comparable, preferably better than that of the dota chelate formed with the same metal.

Inertness with respect to other metals (point c) may be evaluated by determining and comparing the $pCu^{2+}$ versus $pZn^{2+}$. Competitive experiments may also be conducted. Especially, excess of zinc necessary to lead to a transchelation may be determined in competitive experiments with zinc. In the present invention, a chelate is considered having a suitable inertness with respect to other metals when it has inertness at least comparable, preferably better than that of the dota chelate formed with the same metal.

Kinetic inertness (point d) may be evaluated by measuring metal dissociation upon competition with H⁺, in acid medium. Especially, half-life of the complex may be determined in presence of H⁺ at different concentrations and temperatures. In the present invention, a chelate is considered having a suitable kinetic inertness when it is at least comparable, preferably better than that of the dota chelate formed with the same metal.

Stability upon reduction (point e) may be evaluated by determining the dissociation of the reduced metal. Dissociation may be measured with cyclic voltammetry in electrochemical experiments. In the present invention, a chelate is considered having a suitable stability upon reduction when it is at least comparable, preferably better than that of the dota chelate formed with the same metal.

Chelates with a good thermodynamically stability and a kinetic inertness prevent possible transchelation of the metal when the complex is challenged with biological ligands or bioreductants.

It is also important that the chelate and the chelator display good water solubility.

As stated above, the commercially available dota is used to complex $^{64}$Cu(II), $^{67}$Cu(II) and $^{68}$Ga(III). However, copper-dota chelates are far from meeting requirements of the above specifications.

Due to their good affinity with copper (II), tetraazacycloalkanes derivatives of cyclam, such as for example teta and te2a (scheme 1), were recently used to complex $^{64}$Cu or $^{67}$Cu for PET or RIT applications. Their suitable N-functionalization can also give them a good affinity toward other metals such as heavy metal or lanthanides and extend their use in these applications with for example $^{99m}$Tc, $^{186}$Re, $^{188}$Re, $^{111}$In, $^{68}$Ga, $^{89}$Zr, $^{177}$Lu, $^{149}$Tb, $^{153}$Sm, $^{212}$B ($^{212}$Pb), $^{213}$Bi and $^{225}$Ac. However, chelates formed from these derivatives of cyclam do not meet all requirements of the above specifications.

Therefore, there is a need for new ligands enabling to form chelates meeting all the requirements of the specifications mentioned above. Especially, ligands potentially useful for radiopharmaceuticals should combine a high thermodynamic stability and kinetic inertness of the complexes with a fast metal complexation under mild conditions, as the latter is crucial to take full advantage of the short radioisotope half-life times and allow for use of heat- and pH-sensitive biomolecules.

Picolinate arms have been demonstrated to induce strong coordination ability toward transition and post-transition metals when appended on macrocyclic ligands, as well as non macrocyclic ligands. Indeed, picolinate moiety is bidentate: it has a nitrogen atom and an oxygen atom, both capable to participate to the coordination of a metal. Therefore, picolinate derivatives were recently used for the complexation of lanthanides, lead or bismuth (Rodrigez-Rodrigez A. et al. *Inorg. Chem.* 2012, 51, 13419-13429; Rodrigez-Rodrigez A. et al. *Inorg. Chem.* 2012, 51, 2509-2521). They were also recently used for the complexation of copper.

Orvig et coll. disclosed a derivative of ethylenediamine grafted with two picolinate arms H$_2$dedpa, represented on scheme 2 below for the chelation of copper (Boros et al., *JACS,* 2010, 132, 15726-33; Boros et al. *Nucl. Med. Biol.* 2011, 38, 1165-1174).

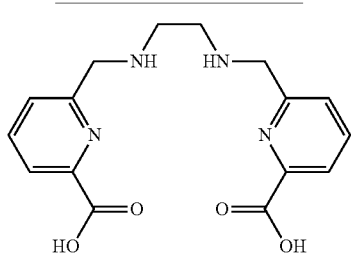

Scheme 2. Structure of H$_2$dedpa.

Derivatives of H$_2$dedpa were also proposed, with various bioconjugation groups (Boros et al. *Inorg. Chem.* 2012, 51, 6279-6284; Bailey et al. *Inorg. Chem.* 2012, 51, 12575-12589; Boros et al. *Nucl. Med. Biol.* 2012, 39, 785-794). However, results were quite disappointing, especially for the coordination of Cu(II), for an application in medicine. Indeed, Cu(II) complexes display low kinetic and thermodynamic stability, as well as decreased serum stability (Boros et al. *Inorg. Chem.* 2012, 51, 6279-6284), thus not meeting requirements b), d) and e) of the above specifications.

In a preliminary work, the Applicant proposed a triaza macrocycle with one picolinate and two picolyl pendant arms, Hno1pa2py (scheme 3), which was found to easily form stable and inert copper(II) complexes as well, and additionally resulted in a very efficient radiolabeling with $^{64}$Cu (Roger et al. *Inorg. Chem.* 2013, 21(9), 5246-5259). Despite promising properties, all the requirements of the above-mentioned specifications were not entirely met: the stability of the formed copper chelate with this ligand needs to be improved, in particular upon the reduction of copper (II) to copper (I) in the physiologic media.

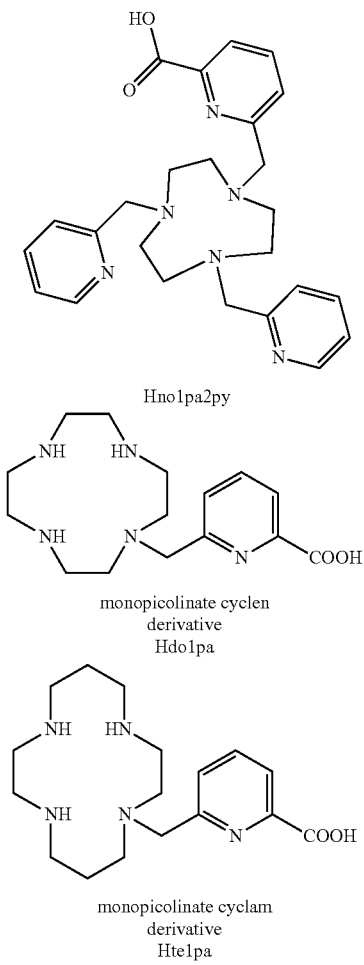

Scheme 3. Applicant's former generations of picolinate-functionalized chelators.

The Applicant then developed picolinate derivatives of cyclen and cyclam (scheme 3), especially a first generation of monopicolinate derivative of cyclam, Hte1pa (Lima et al. *Inorg. Chem.* 2012, 51(12), 6916-6927). The corresponding copper chelate gives good results relative to the requirements a)-c) of the specifications. However, inertness in acidic medium, (point d) of the specifications, and inertness with regard to reduction (point e) were not optimized.

Therefore, the Applicant conducted research to provide a new ligand comprising picolinate arms, overcoming above-mentioned drawbacks, i.e. to improve inertness in acidic medium and inertness in reductive medium, while meeting the other requirements of the specifications mentioned above.

Rigid tetraazamacrocycles, known as "cross-bridged chelators", are the subject of great interest due to the outstanding behavior of their complexes, especially their inertness.

Examples of cross-bridged chelators are cross-bridged cyclam derivatives cb-te2a and side-bridged sb-te1a1p or cross-bridged cyclen derivative cb-do2a (scheme 1). Cross-bridged chelators are defined as containing an ethylene (or propylene) bridging unit connecting two nitrogen atoms of the macrocycle in trans position and they have originated some of the most inert copper (II) complexes ever reported.

Furthermore, successful radiolabeling and bioconjugation of a few examples have also been achieved.

Especially, cross-bridged cb-te2a attracts a great interest since it forms the most inert copper complexes (points d) and e) of above specifications), leading thus to limited if any release of copper in the body.

Therefore, the Applicant considered introducing a cross-bridge in Hte1pa, to form the new ligand Hcb-te1pa, in order to improve inertness:

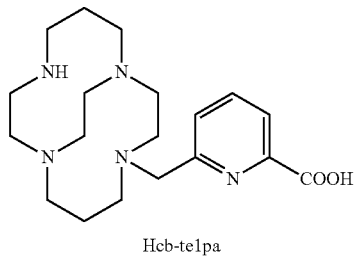 [SMILES: O=C(O)c1cccc(CN2CCCN3CCNCCCN(CC3)CC2)n1]

Hcb-te1pa

However, all constrained bridged chelators described in the art, including Hcb-te2a, are very basic since they are proton-sponges: a proton remains blocked in the macrocyclic cavity due to the structure of the compound, and this proton may not be easily displaced by the metal. This proton-sponge behavior renders metallation kinetics very slow. Drastic conditions are necessary to displace the proton, such as elevated temperatures, which is incompatible when sensible biological vectors are grafted to the chelate to form a bioconjugate.

As a consequence, cross-bridged chelators, and especially Hcb-te2a, meet the above mentioned specifications, especially inertness points d) and e), with the notable exception of a very slow metallation kinetics (point a).

Therefore, by introducing a cross-bridge in Hte1pa to improve inertness, the Applicant expected a drastic decrease of metallation kinetics, leading to a ligand offering a compromise between good inertness and fast kinetics but not meeting all 5 requirements of the above specifications.

As expected, the Applicant demonstrated that, as other cross-bridged derivatives, the Hcb-te1pa ligand of the invention is a proton-sponge (see acido-basic studies—example 5, paragraph B.1).

However and unexpectedly, cross-bridging Hte1pa to form Hcb-te1pa and derivatives thereof did not lead to a decrease of metallation kinetic, compared to non-cross-bridged cyclams. On the contrary, the cross-bridged ligand of the invention Hcb-te1pa surprisingly shows a very rapid metallation kinetic, even in acidic conditions. The metallation occurs quasi instantaneously: for example, more than 90% copper is chelated immediately and remaining copper is chelated within a few seconds (see experimental part—example 5, paragraph B.3). To the knowledge of the Applicant, there is no other case reported in the art of a cross-bridged cyclam or cyclen having a rapid metallation kinetic in aqueous acidic medium and the present invention overcomes a strong prejudice of the skilled artisan.

Without willing to be linked by a theory, it seems that the pre-organized character of the cross-bridged ligand, which was evidenced in crystallographic studies (FIG. 1), together with the presence of a carbonyl group on the aromatic moiety, might be at the origin of this unexpected behavior. It was observed that the structure of the chelate is close to the structure of the ligand (FIG. 2).

The Applicant thus provides a new ligand of formula Hcb-te1pa:

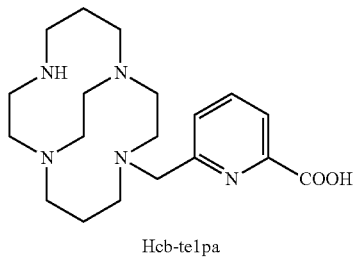

Hcb-te1pa and derivatives thereof, especially derivatives functionalized with coupling functions suitable for grafting vectoring groups or derivatives comprising vectoring groups.

In a preferred embodiment, the invention relates to ligands of formula (I)

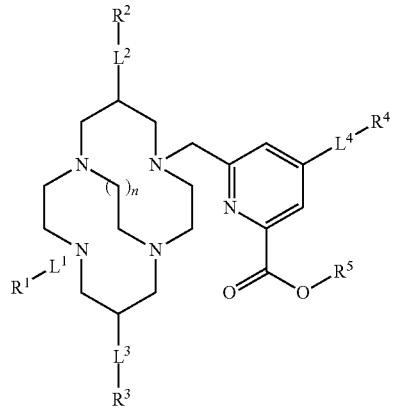

wherein n, $R^1$, $R^2$, $R^3$, $R^4$, $R^5$, $L^1$, $L^2$, $L^3$ and $L^4$ are as defined below.

Upon complexation with metallic cation, the ligands of the invention lead to chelates meeting the 5 requirements of the above specifications. Especially, properties of copper(II) chelate of Hcb-te1pa are reported in the experimental part below and compared to those of copper(II) chelates of the art, evidencing that the chelate of the invention entirely fulfills specifications.

The invention also relates to chelates resulting from the complexation of a ligand of formula (I) with metallic cations.

The ligand of formula (I) of the invention presents the advantage of being easily manufactured using a simple chemical synthesis.

Moreover, the ligand Hcb-te1pa and derivatives thereof present a competency for diverse radioisotopes useful in nuclear medicine, such as for example $^{64}$Cu, $^{67}$Cu, $^{68}$Ga, $^{89}$Zr, $^{99m}$Tc, $^{111}$In, $^{186}$Re, $^{188}$Re, $^{210}$At, $^{212}$Bi ($^{212}$Pb), $^{213}$Bi, $^{225}$Ac, $^{90}$Y, $^{177}$Lb, $^{153}$Sm, $^{149}$Tb or $^{166}$Ho.

The structure of Hcb-te1pa enables the bio-vectorization of the chelate by the introduction of vectorizing groups on the cyclam core, through N-functionalization and/or C-functionalization. Especially, the cyclam core may be C-functionalized according to the method described in patent application WO2013/072491. Moreover, the carboxylic function of the picolinate arm may also be functionalized. The invention thus encompasses Hcb-te1pa ligand, functionalized and/or vectorized derivatives thereof and corresponding chelates with metallic cations, preferably copper (II) or gallium(III).

The chelate of the invention is obtained in aqueous medium, contrary to what is currently done in the art, which is very advantageous for nuclear medicine applications.

Besides applications in nuclear medicine, the ligand of formula (I) of the invention may be used for epuration of effluents contaminated with radioactive elements or metals such as lead; catalysis; solid/liquid extraction and liquid/liquid extraction; or detection of traces of metallic cations.

Definitions

In the present invention, the following terms have the following meanings:
"complex" or "chelate" refer to a molecule binding a metal ion. Chelation (or complexation) involves the formation or presence of two or more separate coordinate bonds between a polydentate (multiple bonded) molecule and a single central atom. Polydentate molecules are often organic compounds, and are called ligands, chelants, chelatants, chelators, chelating agents, or sequestering agents.
"ligand" or "chelator" refer to a polydentate molecule able to form coordinate bonds with a metal ion to give a chelate.
"coupling function" refers to a function capable to react with another function. In a preferred embodiment of the invention, the coupling function is selected from the group comprising amine; isothiocyanate; isocyanate; activated ester such as for example N-hydroxysuccinimide ester, N-hydroxyglutarimide ester or maleimide ester; carboxylic acid; activated carboxylic acid such as for example acid anhydride or acid halide; alcohol; alkyne; halide; azide; siloxy; phosphonic acid; thiol; tetrazine; norbornen; oxoamine; aminooxy; thioether; haloacetamide such as for example chloroacetamide, bromacetamide or iodoacetamide; glutamate; glutaric anhydride, succinic anhydride, maleic anhydride; aldehyde; ketone; hydrazide; chloroformate and maleimide.
"vectorizing group" refers to a chemical group suitable to induce site-specific delivery of the compound once administered. In a preferred embodiment of the invention, the vectorizing group is selected from the group comprising antibody, preferably a monoclonal antibody; hapten, peptide, proteins, sugars, nanoparticle, liposomes, lipids, polyamines such as for example spermine.
"activating function" refers to a chemical moiety capable to render reactive a chemical function. For example, for a carboxylic acid chemical function, an activating function may be N-hydroxysuccinimide, N-hydroxyglutarimide maleimide, halide or anhydride moieties.
"alkyl" refers to any saturated linear or branched hydrocarbon chain, with 1 to 12 carbon atoms, preferably 1 to 6 carbon atoms, and more preferably methyl, ethyl, n-propyl, i-propyl, n-butyl, i-butyl, s-butyl and t-butyl, pentyl and its isomers (e.g. n-pentyl, iso-pentyl), and hexyl and its isomers (e.g. n-hexyl, iso-hexyl).
"alkene" or "alkenyl" refer to any linear or branched hydrocarbon chain having at least one double bond, of 2 to 12 carbon atoms, and preferably 2 to 6 carbon atoms. Examples of alkenyl groups are ethenyl, 2-propenyl, 2-butenyl, 3-butenyl, 2-pentenyl and its isomers, 2-hexenyl and its isomers, 2,4-pentadienyl and the like.
"alkyne" or "alkynyl" refer to refer to any linear or branched hydrocarbon chain having at least one triple bond, of 2 to 12 carbon atoms, and preferably 2 to 6 carbon atoms. Non limiting examples of alkynyl groups are ethynyl, 2-propynyl, 2-butynyl, 3-butynyl, 2-pentynyl and its isomers, 2-hexynyl and its isomers—and the like.
"aryl" refers to refers to a polyunsaturated, aromatic hydrocarbyl group having a single ring (i.e. phenyl) or multiple aromatic rings fused together (e.g. naphtyl) or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Non-limiting examples of aryl comprise phenyl, biphenylyl, biphenylenyl, 5- or 6-tetralinyl, naphthalen-1- or -2-yl, 4-, 5-, 6 or 7-indenyl, 1-2-, 3-, 4- or 5-acenaphtylenyl, 3-, 4- or 5-acenaphtenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.
"arylalkyl" refers to an alkyl group substituted by an aryle group: aryl-alkyl-.
"alkylaryl" refers to an aryl group substituted by an alkyl group: alkyl-aryl-.
"heteroaryl" refers but is not limited to 5 to 12 carbon-atom aromatic rings or ring systems containing 1 to 2 rings which are fused together or linked covalently, typically containing 5 to 6 atoms; at least one of which is aromatic, in which one or more carbon atoms in one or more of these rings is replaced by oxygen, nitrogen and/or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2, 1-b] [1,3] thiazolyl, thieno [3,2-b] furanyl, thieno [3,2-b] thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2, 1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl.
"heteroarylalkyl" refers to an alkyl group substituted by an aryle group: heteroaryl-alkyl-.
"alkylheteroaryl" refers to an aryl group substituted by an alkyl group: alkyl-heteroaryl-.
"thioether" refers to a functional group with the connectivity C—S—C.
"halide" refers to fluoro, chloro, bromo, or iodo. Preferred halo groups are fluoro and chloro.
"oxoamine" refers to a —(C=O)—NH$_2$ group.
"aminooxy" refers to a —O—NH$_2$ group.

"ketone" refers to a functional group with the connectivity C—(C=O)—C.
"hapten" refers to a small molecule that can elicit an immune response only when attached to a large carrier.
"radiopharmaceutical" refers to a radioactive medicinal product. Radiopharmaceuticals are used in the field of nuclear medicine for the treatment of many diseases and/or as tracers for their diagnosis.
"patient" refers a warm-blooded animal, more preferably a human, who/which is awaiting the receipt of, or is receiving medical care or is/will be the object of a medical procedure.
"treat", "treating" and "treatment, as used herein, are meant to include alleviating, attenuating or abrogating a condition or disease and/or its attendant symptoms.
"prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.
"therapeutically effective amount" (or more simply an "effective amount") as used herein means the amount of active agent or active ingredient that is sufficient to achieve the desired therapeutic or prophylactic effect in the patient to which/whom it is administered.
"administration", or a variant thereof (e.g. "administering"), means providing the active agent or active ingredient, alone or as part of a pharmaceutically acceptable composition, to the patient in whom/which the condition, symptom, or disease is to be treated or prevented.
By "pharmaceutically acceptable" is meant that the ingredients of a pharmaceutical composition are compatible with each other and not deleterious to the patient thereof.
"pharmaceutical vehicle" as used herein means a carrier or inert medium used as solvent or diluent in which the pharmaceutically active agent is formulated and/or administered. Non-limiting examples of pharmaceutical vehicles include creams, gels, lotions, solutions, and liposomes.
"about" preceding a figure means plus or less 10% of the value of said figure.

DETAILED DESCRIPTION

Ligand

This invention relates to a picolinate cross-bridged cyclam derivative ligand of formula (I):

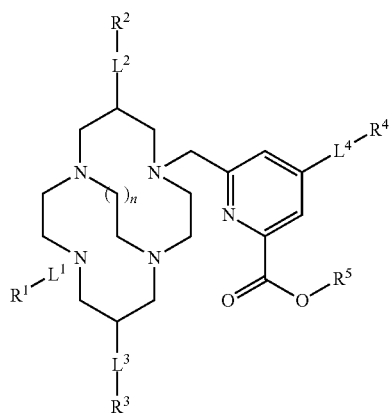

wherein
n is an integer selected from 1 and 2;
$R^1$ represents:
  a hydrogen atom;
  a picolinate arm of formula (II)

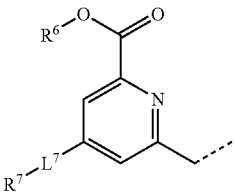

a coupling function, wherein the coupling function is selected from the group comprising amine; isothiocyanate; isocyanate; activated ester such as for example N-hydroxysuccinimide ester, N-hydroxyglutarimide ester or maleimide ester; carboxylic acid; activated carboxylic acid such as for example acid anhydride or acid halide; alcohol; alkyne; halide; azide; siloxy; phosphonic acid; thiol; tetrazine; norbornen; oxoamine; aminooxy; thioether; haloacetamide such as for example chloroacetamide, bromacetamide or iodoacetamide; glutamate; glutaric anhydride, succinic anhydride, maleic anhydride; aldehyde; ketone; hydrazide; chloroformate and maleimide;
  a vectorizing group, wherein the vectorizing group is selected from the group comprising antibody, preferably monoclonal antibody; hapten; peptide; protein; sugar; nanoparticle; liposome; lipid; polyamine such as spermine;
$R^2$, $R^3$, $R^4$ and $R^7$ each independently represent:
  a hydrogen atom;
  a coupling function, wherein the coupling function is selected from the group comprising amine; isothiocyanate; isocyanate; activated ester such as for example N-hydroxysuccinimide ester, N-hydroxyglutarimide ester or maleimide ester; carboxylic acid; activated carboxylic acid such as for example acid anhydride or acid halide; alcohol; alkyne; halide; azide; siloxy; phosphonic acid; thiol; tetrazine; norbornen; oxoamine; aminooxy; thioether; haloacetamide such as for example chloroacetamide, bromacetamide or iodoacetamide; glutamate; glutaric anhydride, succinic anhydride, maleic anhydride; aldehyde; ketone; hydrazide; chloroformate and maleimide;
  a vectorizing group, wherein the vectorizing group is selected from the group comprising antibody, preferably monoclonal antibody; hapten; peptide; protein; sugar; nanoparticle; liposome; lipid; polyamine such as spermine;
$R^5$ and $R^6$ each independently represent:
  a hydrogen atom;
  an activating function, wherein the activating function is selected from the group comprising N-hydroxysuccinimide, N-hydroxyglutarimide and maleimide; halide; —OCOR$^8$ wherein R$^8$ is selected from alkyl, aryl;
  a vectorizing group, wherein the vectorizing group is selected from the group comprising antibody, preferably monoclonal antibody; hapten; peptide; protein; sugar; nanoparticle; liposome; lipid; polyamine such as spermine;

$L^1$, $L^2$, $L^3$, $L^4$ and $L^7$ each independently represent:
  a bond;
  a linker selected from the group comprising alkyl, aryl, arylalkyl, alkylaryl, heteroaryl, heteroarylalkyl, alkylheteroaryl, alkenyl, alkynyl, wherein alkyl moieties are optionally interrupted by one or more heteroatoms selected from O, N and S.

In an embodiment, at least one of $-L^1-R^1$, $-L^2-R^2$, $-L^3-R^3$ and $-L^4-R^4$ is selected from formulae (i), (ii); (iii), (iv) and (v):

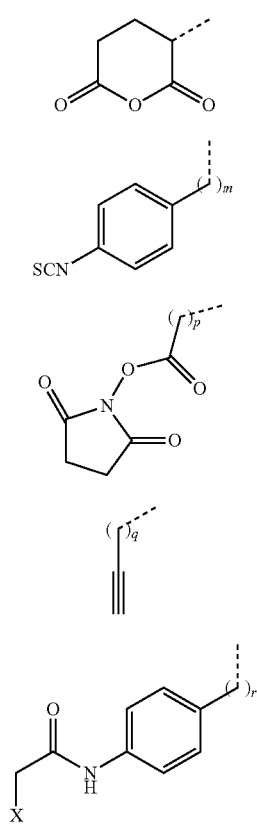

wherein m, p, q and r represent each independently an integer ranging from 0 to 10, preferably 0, 1, 2, 3 or 4 and X represents an halogen, preferably Cl.

In an embodiment, at least one of $-L^1-R^1$, $-L^2-R^2$, $-L^3-R^3$ and $-L^4-R^4$ is selected from formulae (i), (ii); (iii), (iv), (v), (vi) and (vii):

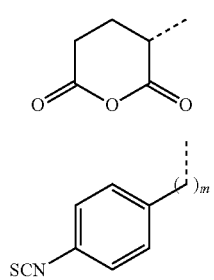

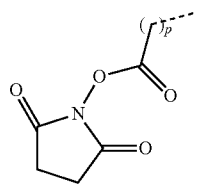

(iii)

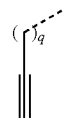

(iv)

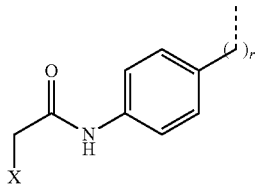

(v)

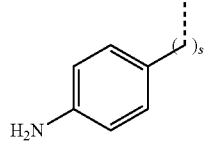

(vi)

(vii)

wherein m, p, q, r, s and t represent each independently an integer ranging from 0 to 10, preferably 0, 1, 2, 3 or 4 and X represents an halogen, preferably Cl.

In one embodiment, the ligand of the invention is of formula (I') or (I")

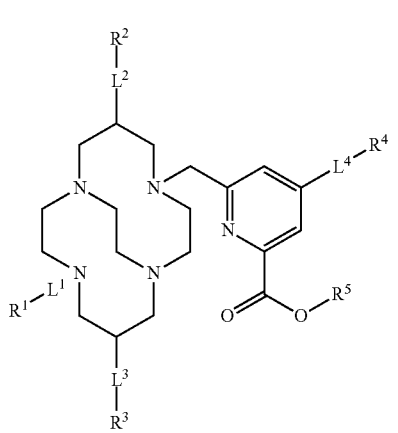

(I')

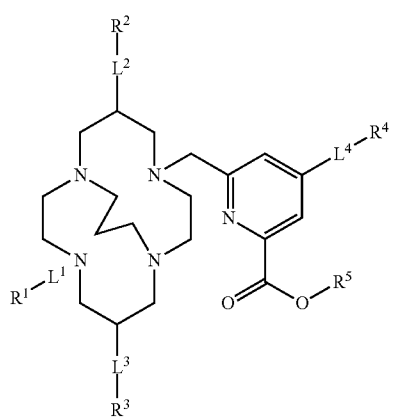
(I″)

wherein $R^1$, $R^2$, $R^3$, $R^4$, $R^5$, $L^1$, $L^2$, $L^3$ and $L^4$ are as defined in formula (I).

In one embodiment, the ligand of the invention is of formula (Ia′) or (Ia″)

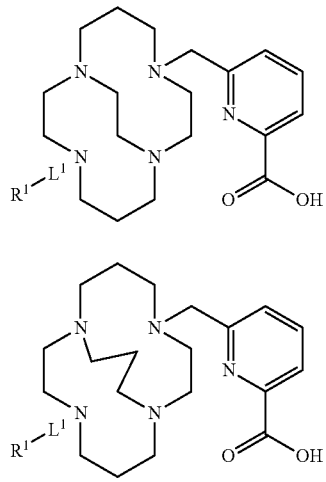
(Ia′)

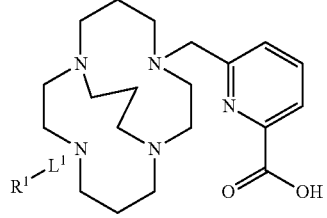
(Ia″)

wherein $R^1$ and $L^1$ are as defined in formula (I).

In an embodiment, -$L^1$-$R^1$ in formula (Ia′) or (Ia″) is preferably selected from formulae (i), (ii); (iii) and (iv):

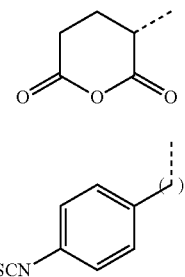
(i)

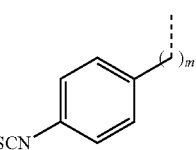
(ii)

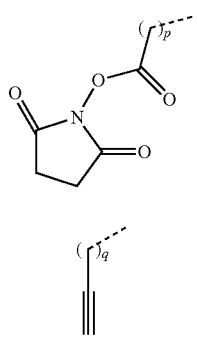
(iii)

(iv)

wherein m, p and q represent each independently an integer ranging from 0 to 10, preferably 0, 1, 2, 3 or 4.

In a specific embodiment, the ligand of the invention is of formula (Ia′-1) or (Ia″-1)

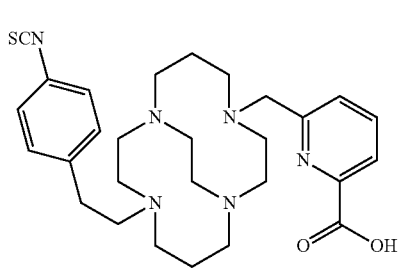
(Ia′-1)

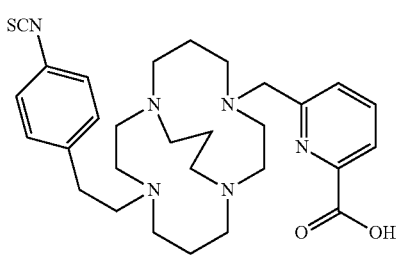
(Ia″-1)

In one embodiment, the ligand of the invention is of formula (Ib-$R^5$) or (Ic-$R^5$)

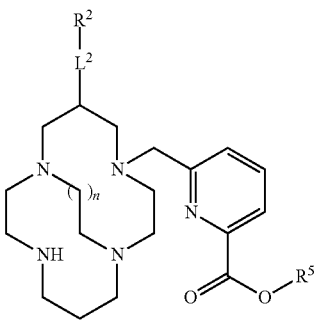
(Ib-$R^5$)

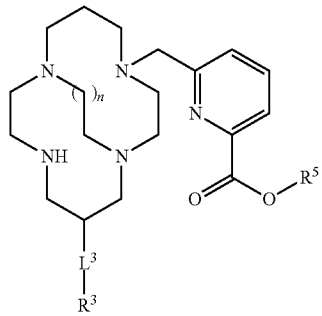

(Ic-R⁵)

wherein $R^2$, $R^3$, $L^2$ and $L^3$ are as defined in formula (I), and n is an integer selected from 1 or 2, preferably n is equal to 1.

In one embodiment, the ligand of the invention is of formula (Ib)

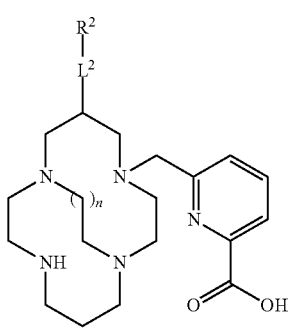

(Ib)

wherein $R^2$ and $L^2$ are as defined in formula (I), and n is an integer selected from 1 or 2, preferably n is equal to 1.

In one embodiment, the ligand of the invention is of formula (Ic)

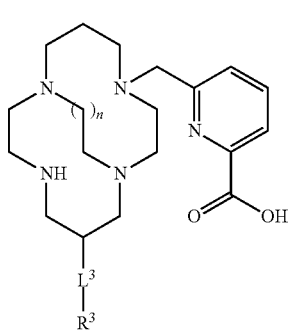

(Ic)

wherein $R^3$ and $L^3$ are as defined in formula (I), and n is an integer selected from 1 or 2, preferably n is equal to 1.

In an embodiment, -$L^2$-$R^2$ in formula (Ib) and -$L^3$-$R^3$ in formula (Ic) are preferably selected from formulae (ii) and (v):

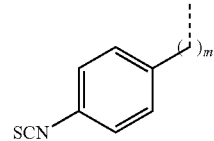

(ii)

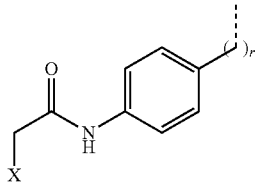

(v)

wherein m and r represent each independently an integer ranging from 0 to 10, preferably 0, 1, 2, 3 or 4 and X represents an halogen, preferably Cl. In a specific embodiment, m is preferably equal to 1 in formula (ii).

In an embodiment, -$L^2$-$R^2$ in formula (Ib) and -$L^3$-$R^3$ in formula (Ic) are preferably of formula (vi) or (vii):

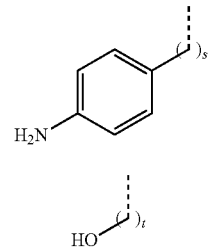

(vi)

(vii)

wherein s and t represent an integer ranging from 0 to 10, preferably 0, 1, 2, 3 or 4, more preferably s is equal to 1 or 2.

Above embodiment relative to preferred definition of -$L^2$-$R^2$ in formula (Ib) and -$L^3$-$R^3$ in formula (Ic) also apply to -$L^2$-$R^2$ in formula (Ib-R⁵) and -$L^3$-$R^3$ in formula (Ic-R⁵).

In one embodiment, the ligand of the invention is of formula (Id') or (Id")

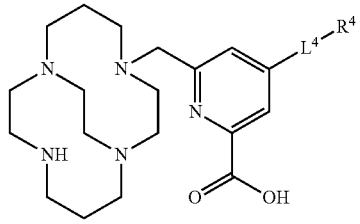

(Id')

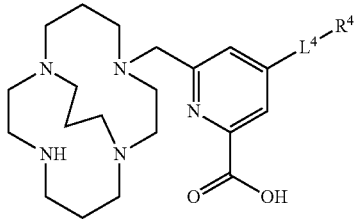

(Id")

wherein $R^4$ and $L^4$ are as defined in formula (I).

In an embodiment, -L⁴-R⁴ in formula (Id') or (Id") is preferably of formula (iv):

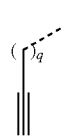
(iv)

wherein q represents an integer ranging from 0 to 6, preferably 0, 1, 2, 3 or 4.

In one embodiment, the ligand of the invention is of formula (Ie') or (Ie")

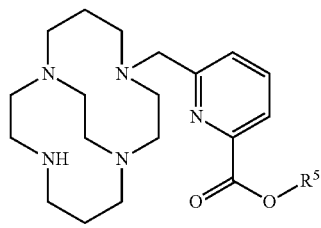
(Ie')

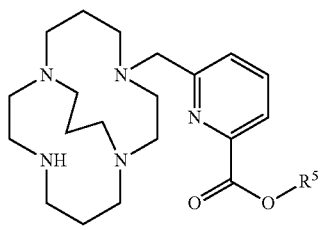
(Ie")

wherein $R^5$ is as defined in formula (I), preferably $R^5$ is an activating function, wherein the activating function is selected from the group comprising N-hydroxysuccinimide, N-hydroxyglutarimide and maleimide; halide; —OCOR⁸ wherein $R^8$ is selected from alkyl, aryl.

In a specific embodiment, the ligand of the invention is of formula "Hcb-te1pa" or "Hpcb-te1pa":

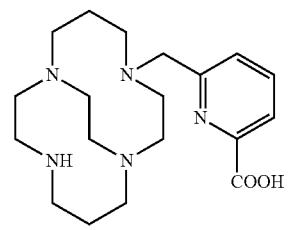

Hcb-te1pa    Hpcb-te1pa

In one embodiment, the ligand of the invention is of formula (If)

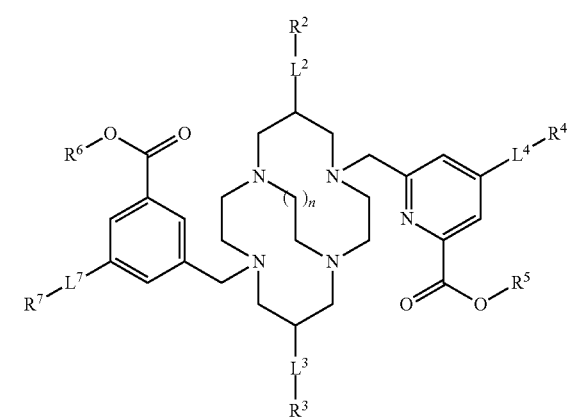

wherein $R^1$, $R^2$, $R^3$, $R^4$, $R^5$, $R^6$, $R^7$, $L^1$, $L^2$, $L^3$, $L^4$ and $L^7$ are as defined in formula (I).

In one embodiment, the ligand of the invention is of formula (If-1') or (If-1")

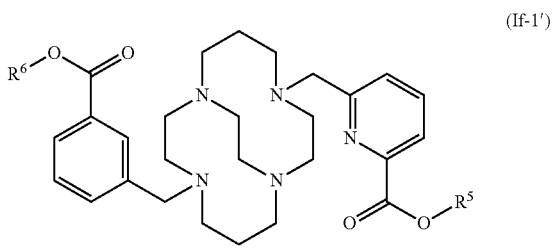
(If-1')

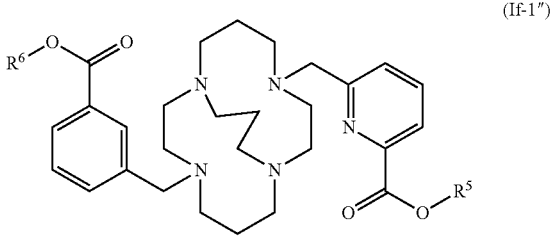
(If-1")

wherein $R^5$ and $R^6$ are as defined in formula (I).

In a specific embodiment, the ligand of the invention is of formula "cb-te2pa" or "pcb-te2pa":

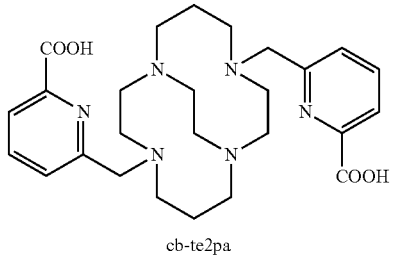

cb-te2pa

-continued

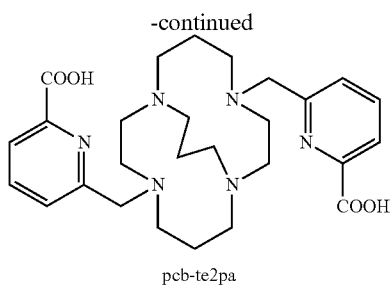

pcb-te2pa

According to a specific embodiment, the ligand of formula (I) of the invention is grafted on nanoparticles.

Particularly preferred compounds of formula (I) of the invention are those listed in Table 1 hereafter.

TABLE 1

| Cpd no | Structure | Chemical name |
|---|---|---|
| Ia'-1 | 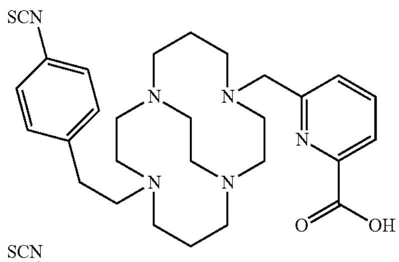 | 6-((11-(4-isothiocyanatophenethyl)-1,4,8,11-tetraazabicyclo[6.6.2]hexadecan-4-yl)methyl)picolinic acid |
| Ia''-1 | 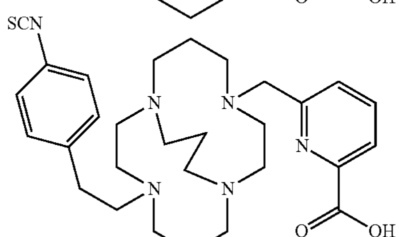 | 6-((11-(4-isothiocyanatophenethyl)-1,4,8,11-tetraazabicyclo[6.6.3]heptadecan-4-yl)methyl)picolinic acid |
| Ib-$R^5$-1 | 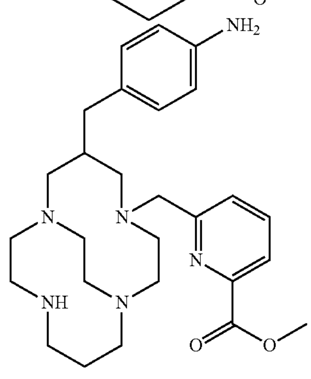 | methyl 6-((6-(4-aminobenzyl)-1,4,8,11-tetraazabicyclo[6.6.2]hexadecan-4-yl)methyl)picolinate |
| Ib-1 | 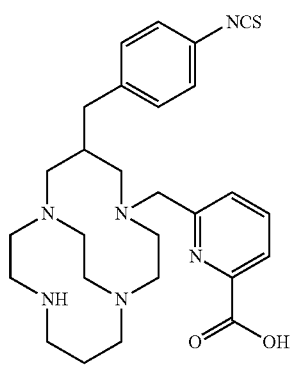 | 6-((6-(4-isothiocyanatobenzyl)-1,4,8,11-tetraazabicyclo[6.6.2]hexadecan-4-yl)methyl)picolinic acid |

TABLE 1-continued

| Cpd no | Structure | Chemical name |
|---|---|---|
| Ib-2 | 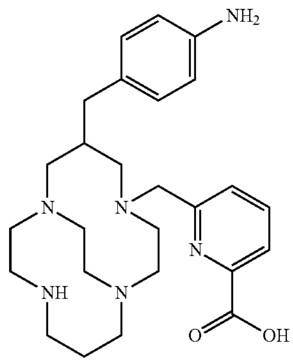 [SMILES: Nc1ccc(CC2CN3CCNCCCN(CC3)CCN(Cc3cccc(C(=O)O)n3)C2)cc1] | 6-((6-(4-aminobenzyl)-1,4,8,11-tetraazabicyclo[6.6.2]hexadecan-4-yl)methyl)picolinic acid |
| Ib-3 | 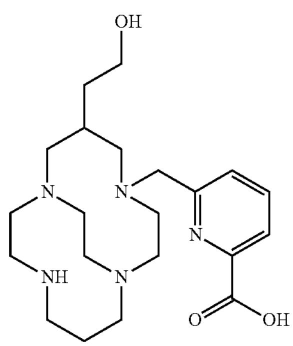 [SMILES: O=C(O)c1cccc(CN2CCN3CCCNCCN(CC3)CC(CCO)C2)n1] | 6-((6-(2-hydroxyethyl)-1,4,8,11-tetraazabicyclo[6.6.2]hexadecan-4-yl)methyl)picolinic acid |
| Ic-R$^5$-1 | 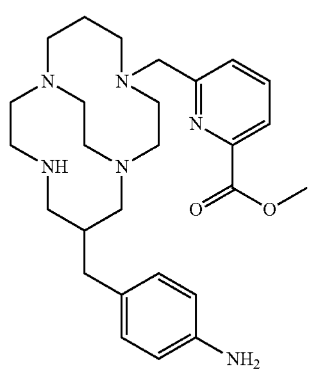 [SMILES: COC(=O)c1cccc(CN2CCCN3CCNCC(Cc4ccc(N)cc4)CN(CC3)CC2)n1] | methyl 6-((13-(4-aminobenzyl)-1,4,8,11-tetraazabicyclo[6.6.2]hexadecan-4-yl)methyl)picolinate |
| Ic-1 | 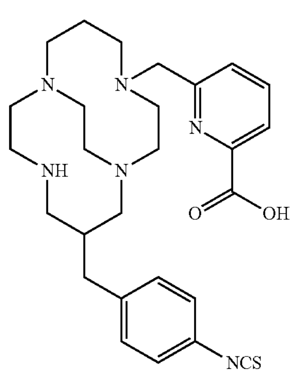 | 6-((13-(4-isothiocyanatobenzyl)-1,4,8,11-tetraazabicyclo[6.6.2]hexadecan-4-yl)methyl)picolinic acid |

TABLE 1-continued

| Cpd no | Structure | Chemical name |
|---|---|---|
| Ic-2 | 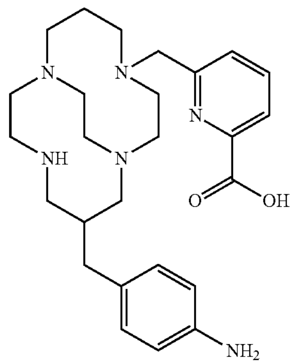 [SMILES: Nc1ccc(CC2CNCCN3CCCN(Cc4cccc(C(=O)O)n4)CCN(CC3)C2)cc1] | 6-((13-(4-aminobenzyl)-1,4,8,11-tetraazabicyclo[6.6.2]hexadecan-4-yl)methyl)picolinic acid |
| Ic-3 | 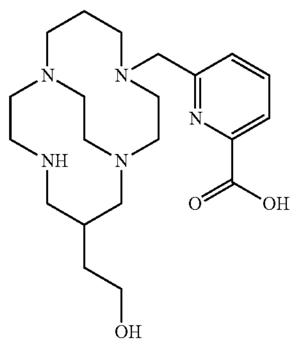 [SMILES: O=C(O)c1cccc(CN2CCCN3CCNCC(CCO)CN(CC3)CC2)n1] | 6-((13-(2-hydroxyethyl)-1,4,8,11-tetraazabicyclo[6.6.2]hexadecan-4-yl)methyl)picolinic acid |
| Hcb-te1pa | 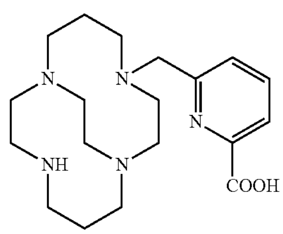 [SMILES: O=C(O)c1cccc(CN2CCCN3CCNCCCN(CC3)CC2)n1] | 6-(1,4,8,11-tetraazabicyclo[6.6.2]hexadecan-4-ylmethyl)picolinic acid |
| Hpcb-te1pa | 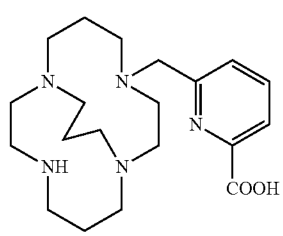 [SMILES: O=C(O)c1cccc(CN2CCCN3CCCN(CCCNCC3)CC2)n1] | 6-(1,4,8,11-tetraazabicyclo[6.6.3]heptadecan-4-ylmethyl)picolinic acid |
| cb-te2pa | 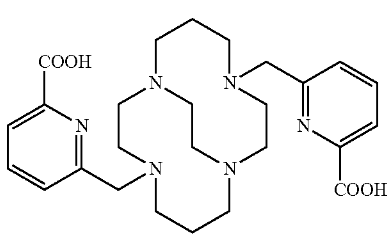 [SMILES: O=C(O)c1cccc(CN2CCCN3CCN(CCCN(Cc4cccc(C(=O)O)n4)CC3)CC2)n1] | 6,6'-(1,4,8,11-tetraazabicyclo[6.6.2]hexadecane-4,11-diylbis(methylene))dipicolinic acid |

TABLE 1-continued

| Cpd no | Structure | Chemical name |
| --- | --- | --- |
| pcb-te2pa | 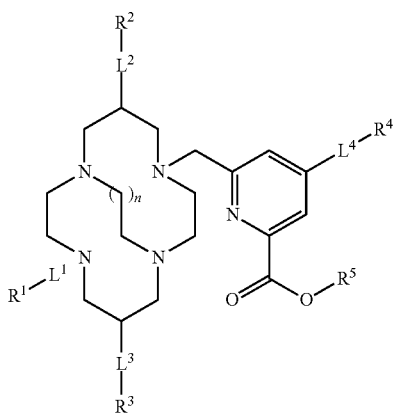 | 6,6'-(1,4,8,11-tetraazabicyclo[6.6.3]heptadecane-4,11-diylbis(methylene))dipicolinic acid |

Chelate

The present invention further relates to a chelate resulting from the complexation of a ligand of the invention of formula (I) and a metallic cation selected from the group comprising copper (II), copper (I), gallium (III), zirconium (IV), technetium (III), indium (III), rhenium (VI), astatine (III), bismuth (III), lead (II), actinium (III), yttrium (III), lutetium (III), samarium (III), terbium (III) or holmium (III).

In an embodiment, the present invention relates to a chelate resulting from the complexation of a ligand of formula (I)

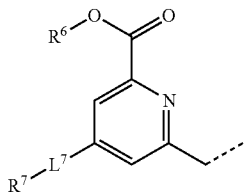

wherein n is an integer selected from 1 and 2;

$R^1$ represents:
- a hydrogen atom;
- a picolinate arm of formula (II)

- a coupling function, wherein the coupling function is selected from the group comprising amine; isothiocyanate; isocyanate; activated ester such as for example N-hydroxysuccinimide ester, N-hydroxyglutarimide ester or maleimide ester; carboxylic acid; activated carboxylic acid such as for example acid anhydride or acid halide; alcohol; alkyne; halide; azide; siloxy; phosphonic acid; thiol; tetrazine; norbornen; oxoamine; aminooxy; thioether; haloacetamide such as for example chloroacetamide, bromacetamide or iodoacetamide; glutamate; glutaric anhydride, succinic anhydride, maleic anhydride; aldehyde; ketone; hydrazide; chloroformate and maleimide;
- a vectorizing group, wherein the vectorizing group is selected from the group comprising antibody, preferably monoclonal antibody; hapten; peptide; protein; sugar; nanoparticle; liposome; lipid; polyamine such as spermine;

$R^2$, $R^3$, $R^4$ and $R^7$ each independently represent:
- a hydrogen atom;
- a coupling function, wherein the coupling function is selected from the group comprising amine; isothiocyanate; isocyanate; activated ester such as for example N-hydroxysuccinimide ester, N-hydroxyglutarimide ester or maleimide ester; carboxylic acid; activated carboxylic acid such as for example acid anhydride or acid halide; alcohol; alkyne; halide; azide; siloxy; phosphonic acid; thiol; tetrazine; norbornen; oxoamine; aminooxy; thioether; haloacetamide such as for example chloroacetamide, bromacetamide or iodoacetamide; glutamate; glutaric anhydride, succinic anhydride, maleic anhydride; aldehyde; ketone; hydrazide; chloroformate and maleimide;
- a vectorizing group, wherein the vectorizing group is selected from the group comprising antibody, preferably monoclonal antibody; hapten; peptide; protein; sugar; nanoparticle; liposome; lipid; polyamine such as spermine;

$R^5$ and $R^6$ each independently represent:
- a hydrogen atom;
- an activating function, wherein the activating function is selected from the group comprising N-hydroxysuccinimide, N-hydroxyglutarimide and maleimide; halide; —$OCOR^8$ wherein $R^8$ is selected from alkyl, aryl;
- a vectorizing group, wherein the vectorizing group is selected from the group comprising antibody, preferably monoclonal antibody; hapten; peptide; protein; sugar; nanoparticle; liposome; lipid; polyamine such as spermine;

$L^1$, $L^2$, $L^3$, $L^4$ and $L^7$ each independently represent:
- a bond;
- a linker selected from the group comprising alkyl, aryl, arylalkyl, alkylaryl, heteroaryl, heteroarylalkyl, alkylheteroaryl, alkenyl, alkynyl, wherein alkyl moieties are optionally interrupted by one or more heteroatoms selected from O, N and S;

with a metallic cation selected from the group comprising copper (II), copper (I), gallium (III), zirconium (IV), technetium (III), indium (III), rhenium (VI), astatine (III), bismuth (III), lead (II), actinium (III), yttrium (III), lutetium (III), samarium (III), terbium (III) or holmium (III).

According to a preferred embodiment, the metallic cation is a radioisotope, preferably a radioisotope selected from the group comprising $^{64}$Cu(II), $^{67}$Cu(II), $^{68}$Ga(III), $^{89}$Zr (IV), $^{99m}$Tc(III), $^{111}$In(III), $^{186}$Re(VI), $^{188}$Re(VI), $^{210}$At (III), $^{212}$Bi ($^{212}$Pb), $^{213}$Bi(III), $^{225}$Ac(III), $^{90}$Y(III), $^{177}$Lu (III), $^{153}$Sm(III), $^{149}$Tb(III) or $^{166}$Ho(III), more preferably $^{64}$Cu (II), $^{67}$Cu(II) or $^{68}$Ga(III).

When the metallic cation is a radioisotope, the chelate of the invention is a radiopharmaceutical.

Preferred embodiments relative to the ligand of formula I described above apply to the chelate of the invention.

Especially, in one embodiment, the ligand of the chelate of the invention is of formula (Ia') or (Ia")

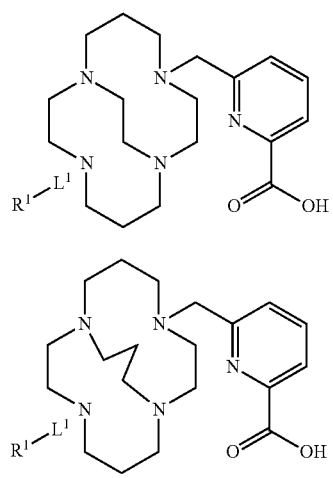

wherein -L$^1$-R$^1$ is selected from formulae (i), (ii); (iii), (iv) and (v):

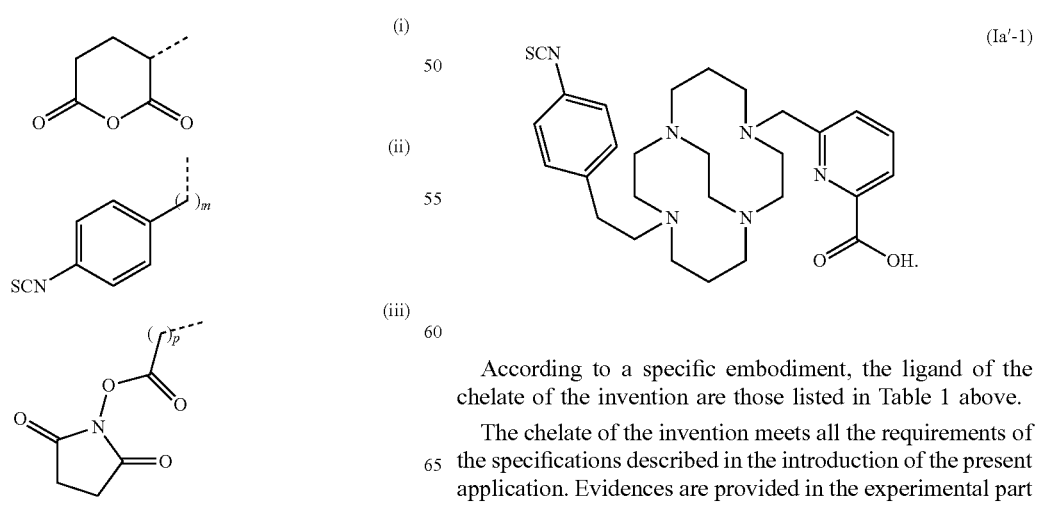

wherein m, p, q and r represent each independently an integer ranging from 0 to 10, preferably 0, 1, 2, 3 or 4 and X represents an halogen, preferably Cl.

According to a specific embodiment, the ligand of the chelate of the invention is of formula Hcb-te1pa:

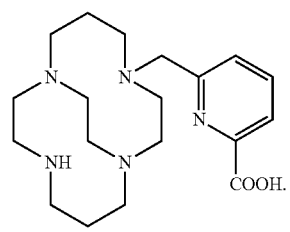 [SMILES: O=C(O)c1cccc(CN2CCCN3CCNCCCN(CC3)CC2)n1]

According to a specific embodiment, the ligand of the chelate of the invention is of formula (Ia'-1)

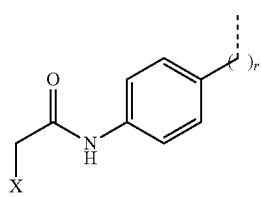

According to a specific embodiment, the ligand of the chelate of the invention are those listed in Table 1 above.

The chelate of the invention meets all the requirements of the specifications described in the introduction of the present application. Evidences are provided in the experimental part below.

Process of Manufacturing—Ligand and Chelate

Synthesis of the Ligand

The present invention further relates to a process for manufacturing the ligand of the invention.

According to one embodiment, the process for manufacturing the ligand of formula (I) of the invention comprises:

reacting compound of formula (i)

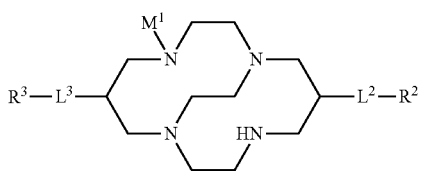

wherein $L^2$, $R^2$, $L^3$ and $R^3$ are as defined in formula (I), $M^1$ represents
  a hydrogen atom,
  an amino-protecting group such as for example a carbobenzyloxy, a p-methoxybenzyl carbonyl, a tert-butoxy carbonyl, a 9-fluorenylmethyloxycarbonyl, a benzoyl, a benzyl, a carbamate group, a p-methoxybenzyl, a 3,4-dimethoxybenzyl, a p-methoxyphenyl, a tosyl, an arylsulphonyl, or any other suitable amino-protecting group known by those skilled in the art,
  -$L^1$-$R^1$, wherein $L^1$ and $R^1$ are as defined in formula (I);

with compound of formula (ii)

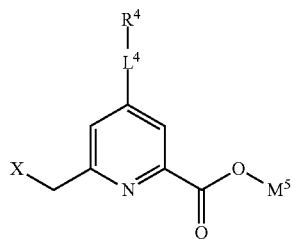

wherein $L^4$ and $R^4$ are as defined in formula (I)

X represents an halogen atom, preferably Cl; and $M^5$ represents
  a protecting group selected from alkyl group, preferably methyl or ethyl, more preferably methyl;
  $R^5$, wherein $R^5$ are as defined in formula (I) provided that it does not represents a hydrogen atom;

to afford compound of formula (iii)

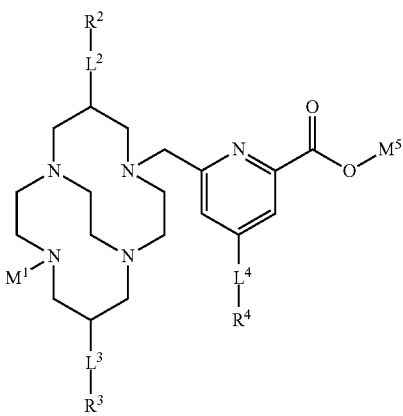

wherein $L^2$, $R^2$, $L^3$, $R^3$, $L^4$ and $R^4$ are as defined in formula (I) and $M^1$ and $M^5$ are as defined above;

and where needed conducting on (iii) one or more subsequent step selected from:

deprotecting the acidic function protected by $M^5$, to afford compound of formula (I) wherein $R^5$ represents a hydrogen atom;

introducing an activating function or a vectorizing group on the acidic function to afford compound of formula (I) wherein $R^5$ represents an activating function or a vectorizing group;

deprotecting the amine function protected by $M^1$, to afford compound of formula (I) wherein -$L^1$-$R^1$ represents —H;

introducing -$L^1$-$R^1$ on the amine function, wherein -$L^1$-$R^1$ is as defined in in formula (I);

to afford compound of formula (I).

According to one embodiment, in the case wherein $M^1$ represents -$L^1$-R1 and $M^5$ represents $R^5$, compound of formula (iii) corresponds to compound of formula (I).

According to a preferred embodiment, the synthetic protocol used for the preparation of the Hcb-te1pa ligand of the invention is described in scheme 4 and consists in two steps starting from the previously described cross-bridged cyclam (i-a) (Wong et al. *J. Am. Chem. Soc.* 2000, 122, 10561-10572) and 6-chloromethylpyridine methyl ester (ii-a) (Mato-Iglesias et al. *Inorg. Chem.* 2008, 47, 7840-7851). Alkylation of the constrained cyclam with the electrophilic derivative in absence of a base affords compound (iii-a). Ester derivative (iii-a) is subsequently hydrolyzed with an aqueous acidic solution to lead quantitatively to Hcb-te1pa, preferably in its hydrochloride salt form.

Scheme 4. Process of manufacturing of Hcb-telpa ligand.

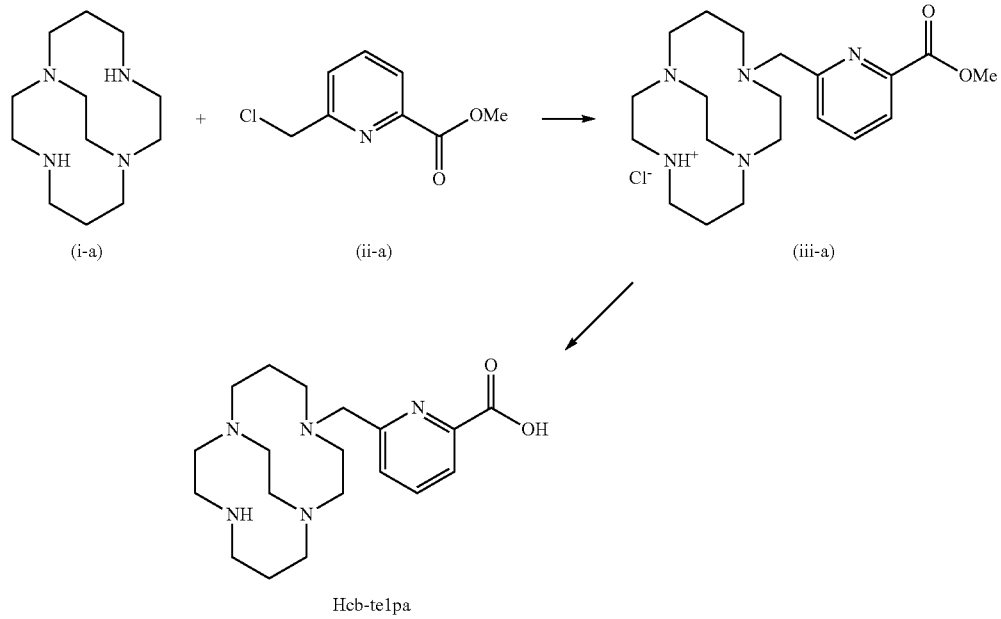

Synthesis of the Chelate

The present invention further relates to a process of manufacturing of the chelate of the invention.

According to one embodiment, the process for manufacturing a chelate according to the invention comprises reacting a ligand of formula (I) according to the invention with a metallic cation selected from the group comprising copper (II), copper (I), gallium (III), zirconium (IV), technetium (III), indium (III), rhenium (VI), astatine (III), bismuth (III), lead (II), actinium (III), yttrium (III), lutetium (III), samarium (III), terbium (III) or holmium (III).

In an embodiment, the process of manufacturing the chelate of the invention comprises reacting the ligand of formula (I) of the invention with a metallic cation in a aqueous medium, preferably by adjusting the pH around neutrality with KOH. The process of the invention is preferably conducted at a temperature ranging from room temperature to reflux, preferably from at room temperature. Chelation process is generally performed for a period ranging from few minutes to 24 hours.

In an embodiment, the metallic cation used in the process the invention is under the form of a salt, preferably perchlorate, chloride, bromide, nitrates, sulfates, acetate, triflate salts.

In a preferred embodiment, the process of manufacturing a copper(II) chelate according to the invention comprises reacting the ligand of formula (I) of the invention with a copper cation in an aqueous solution. In one embodiment, the copper cation is selected from the group comprising $Cu(ClO_4)_2 \cdot 6H_2O$, $Cu_2(OAc)_4$, $CuCl_2$, $Cu(NO_3)_2$, $Cu(OSO_2CF_3)_2$. In a preferred embodiment, the complexation of the copper cation is performed at a pH ranging from 2 to 12, preferably from 2 to 7, more preferably a pH of about 7.

Use of the Chelate

The invention is further directed to the use of the chelates of the invention in nuclear medicine, preferably as imaging agents or medicaments, preferably as radiopharmaceuticals.

The chelates of the invention are useful as imaging agents. In particular, chelates of radioisotopes, preferably chelates of $^{64}Cu$, $^{68}Ga$, $^{89}Zr$, $^{99m}Tc$, $^{111}In$, $^{186}Re$, $^{177}Lu$, $^{153}Sm$, $^{166}Ho$ may be used in PET imaging and/or in SPECT imaging. Chelates of gadolinium (III) may be used in MRI imaging. Chelates of lanthanides, preferably chelates of Eu(III), Tb(III) or Yb(III), may be used for imaging by luminescence.

The chelates of the invention are also useful as medicaments. In particular, chelates of radioisotopes, preferably chelates of $^{67}Cu$, $^{89}Zr$, $^{188}Re$, $^{210}At$, $^{212}Bi$ ($^{212}Pb$), $^{213}Bi$, $^{225}Ac$, $^{90}Y$, $^{153}Sm$ or $^{149}Tb$ may be used in RIT. Depending on the vectorizing group present on the chelate, a broad variety of diseases may be targeted. For example, the following diseases may be targeted using specified vectorizing groups:

|  | Vectorizing group | |
| --- | --- | --- |
| Diseases | name | type |
| lymphomes | anti-CD20 | antibody |
| prostate cancer | anti-CEA | antibody |
|  | bombésine | peptide |
| breast cancer | anti-HER2 | antibody |
| colorectal cancer | anti-EGFR | antibody |
| neuroendocrine tumors | somatostatine analogues such as octréotide, TATE, TOC | peptide |
| tumoral neoangiogenesis | RGD analogues (for integrin targeting) | peptide |

The invention thus provides methods of treatment and/or prevention of diseases, comprising the administration of a therapeutically effective amount of a chelate of the invention, preferably a chelate of a radioisotope, to a patient in need thereof.

The invention further provides the use of a chelate of the invention, preferably a chelate of a radioisotope, for the manufacture of a medicament, preferably a radiopharmaceutical.

According to one embodiment, the chelates of the invention may be administered as part of a combination therapy. Thus, are included within the scope of the present invention embodiments comprising coadministration of a compound of the present invention as active ingredient and additional therapeutic agents and/or active ingredients.

The present invention further relates to a pharmaceutical composition comprising the chelate of the invention in association with at least one pharmaceutically acceptable excipient.

The present invention further relates to a medicament comprising the chelate of the invention.

Generally, for pharmaceutical use, the chelates of the invention may be formulated as a pharmaceutical preparation comprising at least one chelate of the invention and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular, intradermic or subcutaneous injection or intravenous infusion), for intralesional administration, for submucosal administration, for intra-articular administration, for intracavitary administration, for topical administration (including ocular), for artery embolization, for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as salts (especially NaCl), glucose, lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as buffers, antioxidants, lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use.

Use of the Ligand

According to an embodiment, the ligand of the invention is used for the synthesis of a chelate according to the present invention.

According to an embodiment, the ligand of the invention may be used as chelating agent to for chelates which may be used as imaging agents or medicaments in nuclear medicine.

According to an embodiment, the ligand of the invention may be used as scavenging agent.

According to an embodiment, the ligand of the invention is used for depollution of liquid medium by trapping of metallic cations.

According to a specific embodiment, the ligand of the invention may be used in epuration of effluents contaminated with metals. Especially, the ligand of the invention may be used to trap lead or radioactive elements. In a preferred embodiment, the ligand of the invention is used for ultrapurification of liquids. In the present invention, "ultrapurification" refers to the purification of a contaminated solution to a level of contaminant which is much less than 1 ppm (part per million), and generally in the range of ppb (part per billion), ppt (part per trillion), or lower i.e. an ultrapure solution.

According to another embodiment, the ligand of the invention may be used in cation detection, preferably in detection of traces of metallic cations.

According to one embodiment, the ligand and/or the chelate of the invention may be grafted on solid support, such as for example nanoparticules, preferably gold nanoparticles or iron nanoparticles.

According to one embodiment, the ligand and/or the chelate of the invention may be linked to other ligands/chelates, such as for example porphyrines, cyclodextrines, calixarenes or azacycloalkanes.

EXAMPLES

Figure 1:
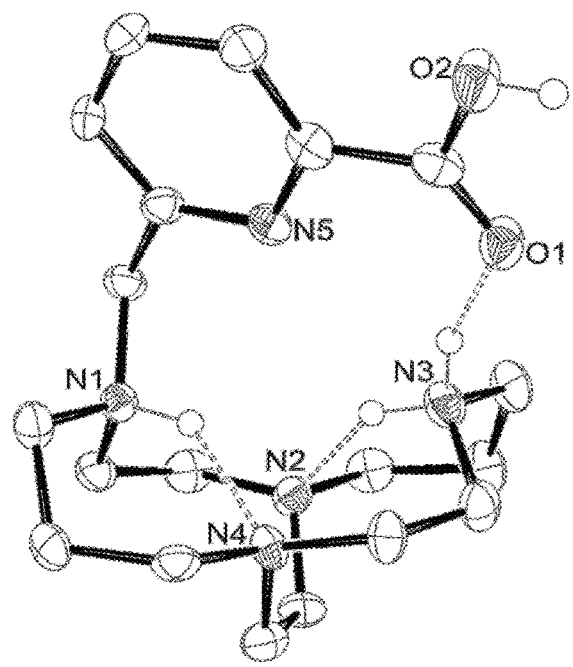
FIG. 1 is a view of X-ray crystal structure of cb-te1pa $(ClO_4)_2$ wherein perchlorate anions and hydrogen atoms bound to carbon atoms are omitted for clarity. The ORTEP plot is at the 30% probability level.

The present invention will be better understood with reference to the following examples. These examples are intended to representative of specific embodiments of the invention, and are not intended as limiting the scope of the invention.

I. Materials and Methods

Reagents were purchased from ACROS Organics and from Aldrich Chemical Co. Cross-bridged cyclam i-a was purchased from CheMatech (Dijon, France) and 6-chloromethyl-pyridine-2-carboxylic acid methyl ester ii-a was synthesized as previously described (Mato-Iglesias, M. Et al. *Inorg. Chem.* 2008, 47, 7840-7851). Elemental analyses were performed at the Service de Microanalyse, CNRS, 69360 Solaize, France. NMR and MALDI mass spectra were recorded at the "Services communs" of the University of Brest. $^1H$ and $^{13}C$ NMR spectra were recorded with Bruker Avance 400 (400 MHz) spectrometer. MALDI mass spectra were recorded with an Autoflex MALDI TOF III smartbeam spectrometer.

When used hereafter, "ca." stands for "calculated".

II. Synthesis of the Ligands

11.1. Synthesis of Hcb-te1pa

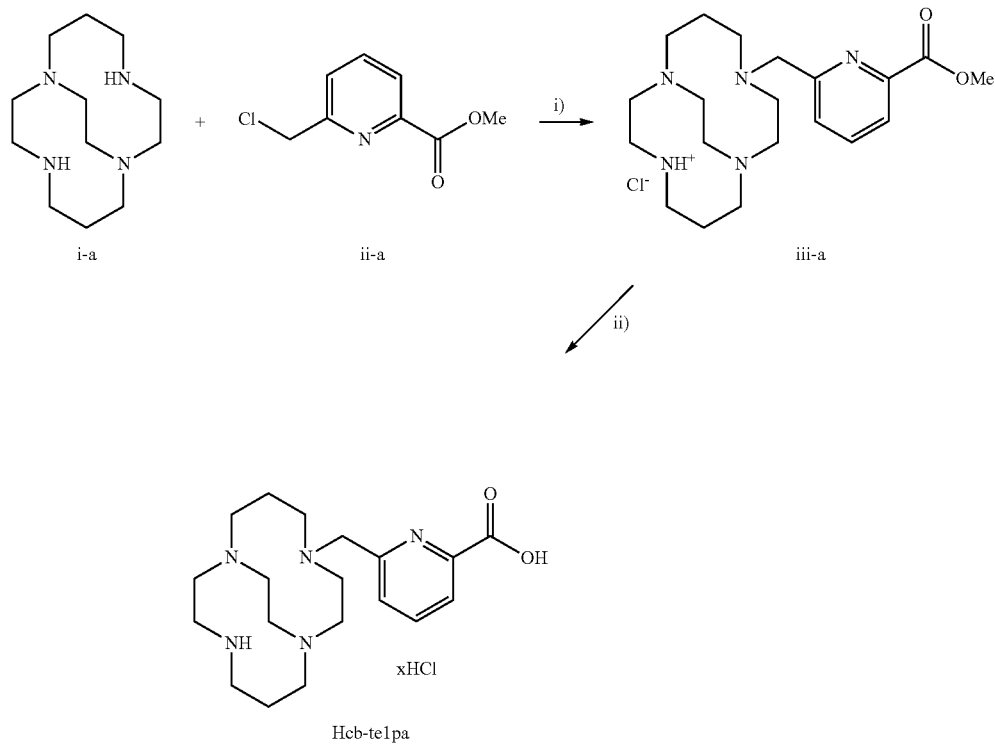

Step i): Mono N-Functionalization of Cross-bridged Cyclam i-a Yielding Compound iii-a.

A solution of 6-chloromethylpyridine-2-carboxylic acid methyl ester ii-a (0.180 g, 0.97 mmol) in 25 mL of distilled acetonitrile was added to a solution of cross-bridged cyclam i-a (0.200 g, 0.88 mmol) in 175 mL of distilled acetonitrile. The mixture was stirred at room temperature overnight. After evaporation of the solvent, the crude product was purified by column chromatography in silica gel (CHCl$_3$/MeOH 8/2) to yield compound iii-a as a colorless oil (0.305 g, 92%).

$^1$H NMR (CDCl$_3$, 400 MHz): 0.95-1.06 (m, 1 H); 1.41-1.55 (m, 1 H); 1.58-1.70 (m, 1 H); 1.83-1.94 (m, 1 H); 2.33-2.64 (m, 8 H); 2.65-2.79 (m, 3 H); 2.80-2.93 (m, 4 H); 2.93-3.06 (m, 3 H); 3.12-3.22 (m; 1 H); 3.46 (d, $^2J$=13.2 Hz, 1 H); 3.48-3.59 (m; 1 H); 3.92 (s, 3 H); 4.08 (d, $^2J$=12.8 Hz, 1 H); 7.52 (d, $^3J$=7.6 Hz, 1 H); 7.90 (dd, $^3J$=8.0 Hz, $^3J$=7.6 Hz, 1 H); 7.98 (d, $^3J$=8.0 Hz, 1 H). $^{13}$C NMR (CDCl$_3$, 100 MHz): 20.5; 25.2; 43.4; 45.7; 48.6; 50.6; 51.0; 52.0; 52.2; 52.3; 54.4; 54.9; 55.9; 62.7; 123.2; 127.9; 138.2; 145.5; 157.8; 164.1. MALDI-TOF (dithranol): m/z=376.25 (M+1). Elem. Anal. Calcd. for C$_{20}$H$_{33}$N$_5$O.HCl.2.8H$_2$O: C, 53.38; H, 8.96; N, 15.56%. Found: C, 53.62; H, 8.69; N, 15.35%.

Step ii): Hydrolysis of Compound 3 Yielding Hcb-te1pa

Hydrochloric acid (20 mL, 6 M) was slowly added to compound iii-a (0.610 g, 1.62 mmol) and the mixture was refluxed overnight. After cooling to room temperature, the solvent was evaporated to yield Hcb-te1pa.4.5HCl3H$_2$O in quantitative yield. Hcb-te1pa is then eluted through an ion-exchange resin with HClO$_4$, preferably 0.1 M HClO$_4$, followed by slow evaporation of the eluted solution to give crystals of H$_3$cb-te1pa(ClO$_4$)$_2$. These crystals are suitable for X-ray diffraction analysis.

$^1$H NMR (D$_2$O, 400 MHz): 1.60 (d, $^2J$=17.2 Hz, 1 H); 1.79 (d, $^2J$=16.4 Hz, 1 H); 2.34-2.51 (m, 2 H); 2.59-2.76 (m, 4 H); 2.85-2.91 (m, 2 H); 3.10-3.70 (m, 13 H); 4.02 (dt, $^3J$=7.6 Hz, $^4J$=4.4 Hz, 1 H); 4.17 (d, $^2J$=13.6 Hz, 1 H); 5.02 (d, $^2J$=14.0 Hz, 1 H); 7.84 (d, $^3J$=7.6 Hz 1 H); 8.17 (dd, $^3J$=8.0 Hz, $^3J$=7.6 Hz, 1 H); 8.34 (d, $^3J$=8.0 Hz, 1 H). $^{13}$C NMR (CDCl$_3$, 100 MHz): 20.8; 21.1; 44.9; 49.9; 51.8; 52.2; 52.7; 56.3; 57.2; 58.1; 59.3; 60.5; 61.1; 129.5; 133.2; 143.0; 151.3; 154.0; 171.7. MALDI-TOF (dithranol): m/z=362.23 (M+1). Elem. Anal. Calcd. for C$_{19}$H$_{35}$N$_5$O$_2$.5HCl.4.5H$_2$O: C, 39.52; H, 7.26; N, 11.21%. Found: C, 36.79; H, 7.22; N, 10.93%.

An ORTEP view of the structure of $H_3$cb-telpa$(ClO_4)_2$ is reported in FIG. 1.

II.2. Synthesis of compound of formula (Ia'-1)

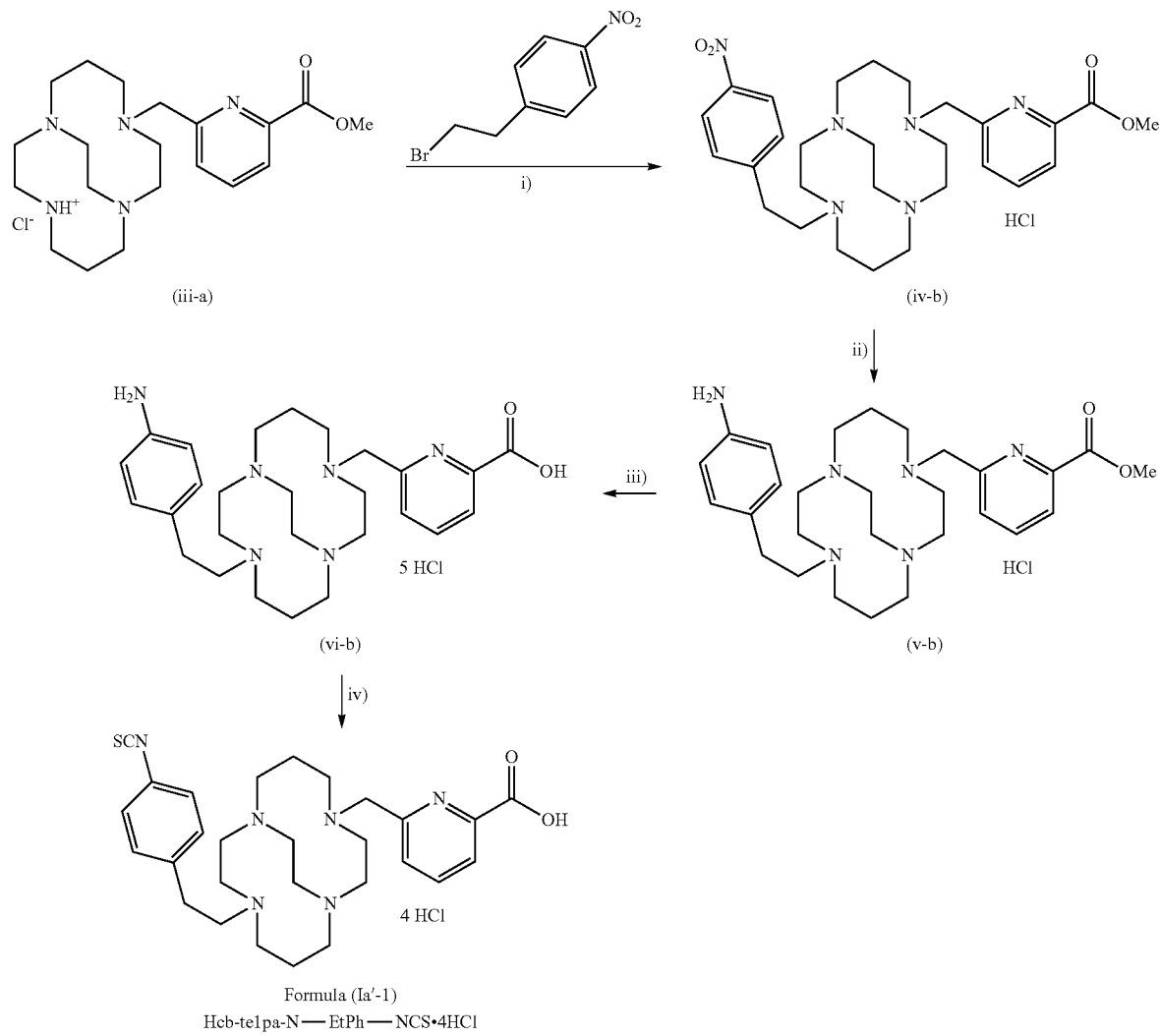

(iii-a)
(iv-b)
(v-b)
(vi-b)

Formula (Ia'-1)
Hcb-telpa-N—EtPh—NCS·4HCl

Step i): Trans-di-N-Functionalization of Cross-bridged Mono-methylpicolinate Cyclam iii-a Yielding Compound iv-b.

4-Nitrophenylethyl bromide (0.968 g, 4.20 mmol) and potassium carbonate (0.872 g, 6.31 mmol) were add to a solution of iii-a (0.865, 2.10 mmol) in 200 mL of distilled acetonitrile. The mixture was refluxed overnight. After evaporation of the solvent, the crude product was purified by column chromatography in silica gel ($CHCl_3$/MeOH 8/2) to yield compound iv-b as a yellow oil (1.000 g, 85%).

$^1$H NMR ($CDCl_3$, 300 MHz): 1.63-1.70 (m, 4 H); 2.50-3.42 (m, 23H); 3.77-3.85 (m, 6 H); 7.41 (d, J=9 Hz, 2 H); 7.43 (d, J=6 Hz, 1 H); 7.72 (t, J=6 Hz, 1 H); 7.86 (d, J=6 Hz, 1 H); 7.86 (d, J=9 Hz, 2 H); 10.50 (S; 1 H). $^{13}$C NMR ($CDCl_3$, 75 MHz): 24.1; 24.5; 30.2; 50.0; 51.6; 51.7; 52.6; 52.8; 53.0; 53.6; 53.9; 54.0; 56.3; 57.7; 58.6; 123.5; 123.8; 127.2; 129.9; 137.5; 146.2; 147.4; 147.6; 157.7; 165.2.

ESI-HRMS: calcd ml z=525.31838 [M+H]$^+$ for $C_{28}H_{41}N_6O_4$. found 525.31838.

Step ii): Reduction of Compound iv-b Yielding v-b.

Tin chloride (1.810 g, 9.55 mmol) and iv-b (0.500 g, 0.95 mmol) were add to a 40 mL solution 1/9 of MeOH/HClaq 12M. The mixture was stirred at room temperature overnight then the excess of HCl was neutralized using potassium carbonate. The desired compound v-b was obtained by extraction with chloroform at pH=14 as yellow oil (420 mg, 83%).

$^1$H NMR ($CDCl_3$, 300 MHz): 1.55 (b s, 4 H); 2.46-3.14 (m, 23 H); 3.69-3.84 (m, 8 H); 6.51 (d, J=9 Hz, 2 H); 6.77 (d, J=9 Hz, 2 H); 7.38 (d, J=6 Hz, 1 H); 7.69 (t, J=6 Hz, 1 H); 7.84 (d, J=6 Hz, 1 H); 10.46 (S; 1 H). $^{13}$C NMR ($CDCl_3$, 75 MHz): 24.0; 24.5; 30.2; 51.0; 51.6; 51.8; 52.2; 52.4; 52.6; 54.0; 54.2; 55.1; 56.3; 56.8; 58.4; 115.2; 123.7; 127.1; 128.5; 129.1; 137.5; 145.1; 147.3; 157.7; 165.3. ESI-HRMS: calcd ml z=495.34475 [M+H]$^+$ for $C_{28}H_{43}N_6O_4$. found 495.34420.

Step iii): Hydrolysis of Compound v-b Yielding vi-b.

Hydrochloric acid (10 mL, 6 M) was slowly added to compound v-b (0.200 g, 0.38 mmol) and the mixture was refluxed overnight. After cooling to room temperature, the solvent was evaporated to yield vi-b as an off-white solid in quantitative yield.

$^1$H NMR (D$_2$O, 300 MHz): 1.63-1.70 (m, 4 H); 2.11-3.68 (m, 28 H); 4.70 (d, J=15 Hz, 1 H); 5.03 (d, J=15 Hz, 1 H); 6.74 (d, J=9 Hz, 2 H); 6.93 (d, J=9 Hz, 2 H); 7.26-7.33 (m, 2 H); 7.56 (t, J=6 Hz, 1 H). $^{13}$C NMR (D$_2$O, 75 MHz): 20.9; 21.4; 28.5; 48.4; 50.9; 60.0; 52.2; 53.2; 55.6; 55.9; 57.4; 57.8; 58.0; 59.2; 60.2; 123.5; 123.8; 127.2; 129.9; 137.5; 146.2; 147.4; 147.6; 157.7; 165.2. ESI-HRMS: calcd ml z=481.32910 [M+H]$^+$ for C$_{27}$H$_{41}$N$_6$O$_4$. found 481.32855.

Step iv): Formation of the isothiocyanate Derivative of Compound vi-b Yielding cb-te1pa-N-EtPh-NCS.

vi-b.5 HCl (100 mg, 0.15 mmol) was dissolved in hydrochloride acid (1 mL, 3 M) then a solution of thiophosgene (0.435 mg, 3.00 mmol) in 1 mL of chloroform was add to the reaction mixture. After an overnight stirring at room temperature, the reaction mixture was washed with chloroform (5×1 mL) by vigorous biphasic stirring followed by decanting of the organic phase to remove excess thiophosgene. Compound cb-te1pa-N-EtPh-NCS was obtained by an overnight lyophilisation as a fluffy off-white solid in quantitative yield.

$^1$H NMR (D$_2$O, 300 MHz): 1.13 (t, J=7.5 Hz, 2 H); 1.64-1.81 (m, 2 H); 2.39-4.01 (m, 26 H); 4.31 (d, J=15 Hz, 1 H); 5.22 (d, J=15 Hz, 1 H); 7.52 (d, J=9 Hz, 2 H); 7.03 (d, J=9 Hz, 2 H); 7.50-7.57 (m, 2 H); 7.82 (t, J=6 Hz, 1 H). $^{13}$C NMR (D$_2$O, 75 MHz): 21.1; 21.5; 28.5; 48.5; 51.2; 52.2; 53.5; 55.7; 56.0; 57.9; 58.2; 59.3; 60.6; 128.4; 129.0; 130.2; 132.0; 132.2; 137.0. 138.1; 141.8; 149.0; 153.7; 169.5. ESI-MS: m/z=523.30 (M+1).

II.3. Synthesis of C-Functionalized Compounds

C-functionalized compounds, especially those of formula (Ib-R$^5$-1), (Ib-1), (Ib-2), (Ib-3), (Ic-R$^5$-1), (Ic-1), (Ic-2) and (Ic-3), may be prepared as described in WO2013/072491, especially as described for compounds of type XVI, and more precisely as described in example 3 for compound (10) (page 30 of WO2013/072491).

II.4. Conjugation of Ib-1 to Trastuzumab

Trastuzumab (4 mg) is added to a solution of Ib-1 (0.53 mg) in 0.1 M Na$_2$CO$_3$ (pH 9.0, 100 µL). The resulting solution is gently agitated at room temperature overnight. The following day, this solution is then placed on a centricon YM-50 (Millipore), and spun down to reduce the volume and washed with PBS (pH 7.4, 2 mL) three times to remove unreacted Ib-1 chelator. The purified Ib-1-trastuzumab conjugate is finely collected in 2 mL of PBS and stored at −20° C.

III. Synthesis of the Chelates

III.1. Complexation of Copper(II) by Hcb-te1pa

Preparation of [Cu(cb-te1pa)]ClO$_4$.

Cu(ClO$_4$)$_2$.6H$_2$O (0.070 g, 0.19 mmol) was added to a solution of Hcb-te1pa.4.5HCl.3H$_2$O (0.100 g, 0.17 mmol) in 10 mL of water, and the pH was adjusted to ≈7 with an aqueous KOH solution. The mixture was heated to 80° C. for 2 h and then stirred overnight at room temperature. Solid impurities were filtered off, and the solution was evaporated to dryness. After addition of acetonitrile, the grey powder was filtered off and the filtrate was evaporated to yield compound [Cu(cb-te1pa)]ClO$_4$ as a blue powder (0.090 g, 83%).

Figure 2:
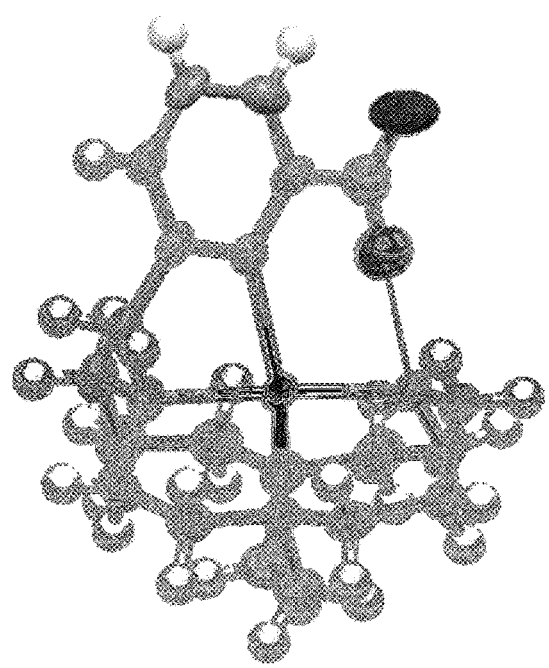
FIG. 2 is a ORTEP view of $[Cu(cb-te1pa)](ClO_4)_2$ wherein perchlorate anions, water molecules and hydrogen atoms bound to carbon atoms are omitted for clarity.

An ORTEP view of the structure of [Cu(cb-te1pa)] (ClO$_4$)$_2$ is shown in FIG. 2.

Complexation of other metallic cation may be conducted by using the same protocol.

III.2. Complexation of $^{64}$Cu or $^{68}$Ga by cb-te1pa

Chelate $^{64}$Cu radiolabeling was achieved by addition of 50 µL $^{64}$CuCl$_2$ solution (40 to 60 MBq; metal composition: 10 ppm of copper for 60 ppm total metals) to a mixture of 50 µL of 0.1 M sodium hydroxide and 500 µL of 1 mM Hcb-te1pa solutions in 0.1 M ammonium acetate. Reaction mixtures were stirred at room temperature (r.t.) during 15 min for Hcb-te1pa. [$^{64}$Cu]acetate was obtained by addition of 50 µL $^{64}$CuCl$_2$ solution to a mixture containing 50 µL of 0.1 M sodium hydroxide and 500 µL of 0.1 M ammonium acetate. Reaction mixture was stirred at r.t. during 30 min. Radiochemical purity of [$^{64}$Cu]cb-te1pa solution was controlled with both TLC and HPLC. [$^{64}$Cu]acetate was taken as reference in the chromatographic system.

Hcb-te1pa was successfully $^{64}$Cu radiolabelled at r.t. in less than 15 min. Both TLC and HPLC chromatograms showed an overall of radiolabelled species of greater than 99% yield. This confirms the results obtained for the complexation of natural copper(II) by Hcb-te1pa. The tests carried out to optimize the labelling also showed that Hcb-te1pa could be radiolabelled even using a 0.01 mM ligand concentration. This demonstrates an important selectivity of Hcb-te1pa for copper(II) over contaminants divalent cations in solution (Fe$^{2+}$, Mg$^{2+}$, Ni$^{2+}$ or Zn$^{2+}$), since the ratio Hcb-te1pa/total metals was below 1.

Chelate $^{68}$Ga radiolabeling was achieved using the same method with appropriate reactants. Hcb-te1pa was successfully $^{68}$Ga radiolabelled and an overall of radiolabelled species of greater than 99% yield was obtained.

III.3. Complexation of $^{64}$Cu by Ib-2

Complexation of $^{64}$Cu with Ib-2 can be achieved by a 30-min preincubation of Ib-2 (100 µg) in EtOH with an excess of Cs$_2$CO$_3$ at 90° C. with constant stirring. Following centrifugation, $^{64}$CuCl$_2$ is added to the isolated supernatant. The mixture is vortexed and incubated at 90° C. for 30 min. The mixture is centrifuged, and the isolated supernatant is evaporated. The dried mixture is dissolved in water, and passed through the 0.2 µm Nylon Acrodisk 13 filter. Formation of $^{64}$Cu-Ib-2 complexes can be verified by radio-TLC using a mobile phase consisting of MeOH:10% ammonium acetate (1:1) on silica plates. Radio-HPLC analysis of $^{64}$Cu-Ib-2 can be accomplished using Xbridge C18 column (4.6×150 mm, 5 µm) with an isocratic method (0.1% TFA in water:MeOH (96:4), 1 mL/min flow rate).

III.4. Complexation of $^{64}$Cu by Ib-1-trastuzumab $^{64}$Cu (0.5-2 mCi) in 0.1 M NH$_4$OAc buffer (pH 8.0, 100 µL) is added to 80 µg of Ib-1-trastuzumab (cf paragraph 11.4 above) in 0.1 M NH$_4$OAc buffer (pH 8.0, 100 µL) or simple distilled water. The reaction mixture is incubated at 25° C. for 10 min, then 50 µg of DTPA is added and the reaction mixture is further incubated for 20 min at 30° C. The radiochemical yield can be checked with instant thin layer chromatography (ITLC-SG, saline). The $^{64}$Cu-labeled Ib-1-trastuzumab is purified by centrifugation using YM-50 filter to remove any $^{64}$Cu-DTPA complexes. Radiochemical purity can be determined by size exclusion high-performance liquid chromatography (Bio Silect SEC 250-5 300× 7.8 mm; flow rate 1 mL/min, with the isocratic mobile phase consisting of PBS, pH 7.4).

Specific Activity Determination of $^{64}$Cu-Ib-1-Trastuzumab

The fixed amount of $^{64}$Cu (220 µCi) in 0.1 M NH$_4$OAc buffer (pH 8.0, 100 µL) is added to various concentrations (1-80 µg) of Ib-1-trastuzumab in 0.1 M NH$_4$OAc buffer (pH 8.0, 100 µL). The reaction mixture is incubated at 25° C. for 10 min, then 50 µg of DTPA is added and the reaction mixture is further incubated for 20 min at 30° C. The radiochemical yield is checked with instant thin layer chromatography (ITLC-SG, saline). Three concentrations of Ib-1-trastuzumab showing 40-90% radiolabeling yield can be used to calculate the specific activity of $^{64}$Cu-labeled Ib-1-trastuzumab.

IV. Physicochemical Properties of Copper(II) Complex of Hcb-te1pa

IV.A. Methods

IV.A.1. Potentiometric Studies

Equipment and work conditions. The potentiometric setup has been described in Roger, M. et al. *Inorg. Chem.* 2013, 52, 5246-5259. The titrant was a KOH solution prepared at ca. 0.1 M from a commercial ampoule of analytical grade, and its accurate concentration was obtained by application of the Gran's method upon titration of a standard HNO$_3$ solution (Rossotti, F. J. and Rossotti, H. *J. J. Chem. Educ.* 1965, 42, 375-378). Ligand solutions were prepared at about $2.0\times10^{-3}$ M, and the Cu$^{2+}$ and Zn$^{2+}$ solutions at ca. 0.05 M from analytical grade nitrate salts and standardized by complexometric titrations with H$_4$edta (ethylenediaminetetraacetic acid). Sample solutions for titration contained approximately 0.04 mmol of ligand in a volume of 30 mL where the ionic strength was kept at 0.10 M using KNO$_3$ as background electrolyte. Metal cations were added at 0.9 equiv. of the ligand amount in complexation titrations. Batch titrations were prepared in a similar way but with each titration point corresponding to ¹⁄₁₀ of the amount of a conventional titration sample. Batch titration points were incubated in tightly closed vials at 25° C. until potential measurements attained complete stability, which happened within a week.

Measurements. All measurements were carried out at 25.0±0.1° C. under inert atmosphere. The electromotive force of the sample solutions was measured after calibration of the electrodes by titration of a standard HNO$_3$ solution at $2.0\times10^{-3}$ M in the work conditions. The [H$^+$] of the solutions was determined by measurement of the electromotive force of the cell, $E=E^{\circ\prime}+Q \log [H^+]+E_j$. The term pH is defined as $-\log [H^+]$. $E^{\circ\prime}$ and Q were determined from the acid region of the calibration curves. Deviations from the Nernst law at very low pH (pH<2.5) were corrected with the VLpH software (Calibration software from the maker of Hyperquad available for free at http://www.hyperquad.co.uk/), which performs a [H$^+$] correction based on a very low pH calibration procedure. The liquid-junction potential, $E_j$, was otherwise found to be negligible for pH >2.5 under the experimental conditions used. The value of $K_w=[H^+][OH^-]$ was found to be equal to $10^{-13.78}$ by titrating a solution of known [H$^+$] at the same ionic strength in the alkaline pH region, considering E° ' and Q valid for the entire pH range. Each titration consisted of 80-100 equilibrium points in the range of pH 2.5-11.5 (or 1.5-11.5 for Cu$^{2+}$ complexations), and at least two replicate titrations were performed for each particular system.

Calculations. The potentiometric data were refined with the Hyperquad software, and speciation diagrams were plotted using the HySS software. The overall equilibrium constants $\beta_i^H$ and $\beta_{MmHhL1}$ are defined by $\beta_{MmHhL1}=[M_m H_h L_l]/[M]^m[H]^h[L]^l$ ($\beta_i^H=[H_hL_l]/[H]^h[L]^l$ and $\beta_{ML-1L}=\beta_{ML(OH)}\times K_w$). Differences in log units between the values of protonated (or hydrolysed) and non-protonated constants provide the stepwise (log K) reaction constants (being $K_{MmHhL1}=[M_m H_h L_l]/[M_m H_{h-1} L_l][H]$). The errors quoted are the standard deviations calculated by the fitting program from all the experimental data for each system.

IV.A.2. Kinetics Studies

Complex Formation. The formation of the copper(II) complex of Hcb-te1pa was studied in buffered aqueous solutions at 25° C. The increasing intensity of the complex d-d transition band in the visible range (600 nm) was followed at pH=5.0 (0.2 M potassium acetate buffer) and pH=7.4 (0.2 M HEPES buffer), with [Cu$^{2+}$]=[Hcb-te1pa]= 0.8 mM. Additionally, complex formation was also studied at pH=3.0 (0.2 M (K,H)Cl) under pseudo-first order conditions, by following the increasing charge transfer band in the UV range (at 310 nm) at [Cu$^{2+}$]=10×[Hcb-te1pa]=2 mM.

Complex Dissociation. The acid-assisted dissociation of the copper(II) complex of Hcb-te1pa was studied under pseudo-first order conditions in 5 M HCl or 5 M HClO$_4$ aqueous solutions containing the complex at $1.0\times10^{-3}$ M. Concentrated acid was added to sample solutions containing preformed complex without control of ionic strength, and the reaction was followed by the decreasing intensity of the complex d-d transition band, at the temperature of 20, 25, 37, 60, and 90° C. in HCl, and at 25° C. in HClO$_4$.

IV.A.3. Electrochemical Studies

Cyclic voltammograms were measured using Autolab equipment at room temperature. All measurements were made using a three-electrode system: a glassy-carbon electrode as a working electrode, a platinum wire as a counter-electrode, and a saturated calomel reference electrode. All electrochemical experiments were performed in ca. 1 mM aqueous solutions of preformed complex under a N$_2$ atmosphere containing 0.1 M NaClO$_4$ as the supporting electrolyte. From the initial potential of the analysis (0 V), the voltage was ramped to −1.3 V, then to 0.2 V, and back to 0 V at a scan rate of 100 mV/s. All potentials are expressed relative to the saturated calomel electrode (SCE) except otherwise noted.

IV.B. Results and Discussion

IV.B.1. Acid-Base Properties of Hcb-te1pa

The protonation constants of Hcb-te1pa were studied in aqueous solution at 25.0° C. The compound has five basic centers consisting of the four amines and the carboxylate function, from which only two could be accurately determined by potentiometric titrations (Table 1). Results obtained for Hcb-te1pa are compared with those of two other tetraazacycloalkalnes: te1pa and cb-cyclam.

The proton-sponge behavior of cross-bridged tetraaza macrocyclic compounds is well known, corresponding to the very high value of the first protonation constant. For Hcb-te1pa, such behavior was verified by $^1$H NMR spectroscopic titration in D$_2$O in the basic pH range. While there are marked resonance shifts in the range of pD=8-12, corresponding undoubtedly to the second protonation constant of the compound (see below), there are no shifts of resonances in the range of pD=12-14, and minor shifts start to be visible only above pD=14. It is thus clear that only at pD >14 the last deprotonation step takes place. However, the spectroscopic data that could be obtained for the highest pH values do not allow for determination of the first protonation constant, as only the beginning of the deprotonation process was detected. Therefore, a value of 15 was postulated for the first protonation constant, which was subsequently used as a constant in all other thermodynamic equilibrium determinations. This particularly high protonation constant must correspond to protonation of one of the macrocyclic amines, and should be highly influenced by hydrogen bonding interactions as is usual in related compounds with relatively small and partially closed structural cavities.

The remaining protonation constants of Hcb-telpa were determined by conventional potentiometric titrations in aqueous solution and at 0.10 M $KNO_3$ ionic strength. The second constant (log K=10.13) must correspond to the protonation of a second macrocyclic amine, while the third one (log K=2.43) should correspond to protonation of the carboxylate group, as observed in the solid state structure of $H_3$cb-telpa$(ClO_4)_2$ described above. No other protonation constants could be calculated, meaning that additional protonation equilibrium may only happen at pH<2.

TABLE 1

Overall ($\beta_i^H$) and stepwise ($K_i^H$) protonation constants, in log units, for Hcb-telpa and related compounds, at 25.0° C. in 0.10M $KNO_3$.

| Equilibrium reaction [a] | L = cb-telpa⁻ [b] | L = telpa⁻ [c] | L = cb-cyclam [d] |
|---|---|---|---|
| | log $\beta_i^H$ | | |
| L + H⁺ ⇌ HL | >15 | 11.55 | 12.42 |
| L + 2 H⁺ ⇌ H₂L | 25.13(5) | 21.66 | 22.61 |
| L + 3 H⁺ ⇌ H₃L | 27.56(5) | 24.37 | (20.23) |
| L + 4 H⁺ ⇌ H₄L | <29.56 | 26.07 | 24.00 |
| | log $K_i^H$ | | |
| L + H⁺ ⇌ HL | >15 | 11.55 | 12.42 |
| HL + H⁺ ⇌ H₂L | 10.13 | 10.11 | 10.20 |
| H₂L + H⁺ ⇌ H₃L | 2.43 | 2.71 | — |
| H₃L + H⁺ ⇌ H₄L | <2.0 | 1.7 | 1.39 |

[a] L denotes the ligand in general; charges are omitted for simplicity.
[b] Values in parentheses are standard deviations in the last significant figures.
[c] From Lima, L. M. P. Et al. *Inorg. Chem.* 2012, 51, 6916-6927.
[d] From ref. Sun, X. et al. *J. Med. Chem.* 2002, 45, 469-477, with I = 0.1M in KCl.

IV.B.2. Thermodynamic Stability of the Metal Complexes of Hcb-telpa

This part corresponds to points b) and c) of the specifications mentioned above.

The stability constants of the complexes formed by Hcb-telpa with $Cu^{2+}$ and $Zn^{2+}$ were determined by potentiometric titrations in aqueous solution at 25.0° C. in 0.10 M $KNO_3$ ionic strength (Table 2). Results obtained for Hcb-telpa are compared with those of two other tetraazacycloalkalnes: telpa and cb-cyclam.

The equilibrium of formation of the copper(II) and especially the zinc(II) complexes is slow in the acidic pH range. In the case of $Cu^{2+}$, the complexation is almost complete from low pH but relatively slow up to pH=4. To overcome this double problem, conventional titrations were performed at pH values below 2 in order to observe a significant percentage of free metal ion (at least 18%) and thus allow for determination of the corresponding stability constant, while giving the solution enough time to reach equilibrium prior to the start of the titration. During titrations, each experimental point included a supplementary equilibration time in order to yield fully stabilized measurements. In the case of $Zn^{2+}$, there is essentially no complexation below pH=4, and in the range of pH=4-6 the complexation is extensive but very slow, taking up to one week for reaching the final equilibrium. For this reason, batch titrations were prepared in the range of pH=4-6 and were left to equilibrate until full stabilization, while conventional titrations were used for the remaining pH regions.

TABLE 2

Overall ($\beta_{MLHh}$) and stepwise ($K_{MLHh}$) stability constants, in log units, for complexes of Hcb-telpa and related ligands with $Cu^{2+}$ and $Zn^{2+}$ cations, at 25.0° C. in I = 0.10M $KNO_3$.

| Equilibrium reaction [a] | L = cb-telpa⁻ [b] | L = telpa⁻ [c] | L = cb-cyclam [d] |
|---|---|---|---|
| | log $\beta_{MLHh}$ | | |
| Cu²⁺ + L ⇌ CuL | 26.00(5) | 25.5 | 27.1 |
| Cu²⁺ + H⁺ + L ⇌ CuHL | — | 27.67 | — |
| Cu²⁺ + L ⇌ CuLOH + H⁺ | — | 14.35 | — |
| Zn²⁺ + L ⇌ ZnL | 18.83(6) | 18.86 | — |
| Zn²⁺ + H⁺ + L ⇌ ZnHL | — | 21.38 | — |
| Zn²⁺ + L ⇌ ZnLOH + H⁺ | 7.50(7) | 7.84 | — |
| | log $K_{MLHh}$ | | |
| Cu²⁺ + L ⇌ CuL | 26.00 | 25.5 | 27.1 |
| CuL + H⁺ ⇌ CuHL | — | 2.17 | — |
| CuLOH + H⁺ ⇌ CuL | — | 11.15 | — |
| Zn²⁺ + L ⇌ ZnL | 18.83 | 18.86 | — |
| ZnL + H⁺ ⇌ ZnHL | — | 2.52 | — |
| ZnLOH + H⁺ ⇌ ZnL | 11.33 | 11.02 | — |

[a] L denotes the ligand in general; charges are omitted for simplicity.
[b] Values in parentheses are standard deviations in the last significant figures.
[c] From Lima, L. M. P. Et al. *Inorg. Chem.* 2012, 51, 6916-6927.
[d] From ref. Sun, X. et al. *J. Med. Chem.* 2002, 45, 469-477, by spectrophotometric competition without ionic strength control.

The speciation is notably simple with both $Cu^{2+}$ and $Zn^{2+}$; the fully deprotonated complex is the single species in the intermediate pH range, and a zinc(II) hydroxo complex can only be found at very basic pH. For a correct comparison of the thermodynamic stability of the complexes of Hcb-telpa with the corresponding values of other ligands from the literature, the pM values that take into account the variable basicity properties of different ligands were also calculated (Table 3). Both the stability constants obtained and the pM values calculated demonstrate a very high thermodynamic stability of the copper(II) complex of Hcb-telpa. Importantly, they also show a very high selectivity of Hcb-telpa for copper(II) complexation over zinc(II). Although the other two ligands taken for comparison exhibit larger pCu values, the value obtained for the copper(II) complex of Hcb-telpa is still high enough for a very strong coordination of $Cu^{2+}$ and to avoid potential transchelation. The thermodynamic stability is not the only important criterion to determine the efficiency of metal complexation because, depending on the application, other factors such as kinetic inertness or in vivo stability can be more important.

TABLE 3

Calculated pM [a] values for the complexes of Hcb-telpa and related compounds.

| Metal ion | Hcb-telpa | Htelpa | cb-cyclam |
|---|---|---|---|
| Cu²⁺ | 15.67 | 18.64 | 19.29 |
| Zn²⁺ | 8.50 | 12.00 | — |

[a] Values calculated at pH = 7.4 for 100% excess of ligand with $[M^{2+}]_{tot} = 1 \times 10^{-5}$ M, based on the presented stability constants.

IV.B.3. Formation and Dissociation of the Copper(II) Complex

This part corresponds to points a) and d) of the specifications mentioned above.

Rapid complexation kinetics are essential for a facile formation of the copper(II) complex. Therefore, some of the most inert cross-bridged complexes may be useless for medical applications given the rather harsh conditions (typically very high temperature and/or high pH) required to achieve near quantitative metal complexation within reasonable time with respect to the limited life time of the radioisotopes.

The copper(II) complex formation with Hcb-te1pa was spectroscopically monitored in different buffered solutions from acidic to neutral pH. In equimolar metal-to-ligand ratio, the complex formation is instantaneous at physiological pH (7.4) and is extremely fast at pH=5, reaching completion (>99%) within a few seconds in the first case and within ca. 3 minutes in the latter case. The reaction becomes progressively slower because of the increase of the acidity of the reaction media, enabling a kinetic study under pseudo-first order conditions using conventional UV-vis spectroscopic methods. In this work such kinetic study was performed at pH=3, which is at the lower limit of the pH range in which the copper(II) complexation is approximately complete under equilibrium in equimolar metal-to-ligand conditions. The data obtained for this reaction under pseudo-first order conditions using an excess of 10 equivalents of metal cation resulted in a formation half-time ($t_{1/2}$) of 1.7 minutes and showed that formation is quantitative (>99%) within ca. 10 minutes.

According to these results, Hcb-te1pa is, to the best of the Applicant's knowledge, the cross-bridged ligand endowed with the fastest complexation ability for copper(II) under very mild conditions. Without willing to be linked by a theory, this performance might be, at least partly, explained by analysis of the crystallographic structure of the free ligand (FIG. 1). Indeed, the pre-organization of the ligand is favored by a hydrogen bond between the acid function of the picolinate and the secondary amine of the macrocycle. The nitrogen atom of the picolinate arm is located just outside of the macrocyclic pocket in favorable position for the coordination to copper(II), which should thus be easily chelated by the five amine functions of the ligand.

The slow dissociation of complexes is probably the most important feature to be taken in consideration when selecting compounds to be used in medical applications. The kinetics of acid-assisted dissociation of the copper(II) complex of Hcb-te1pa were studied under pseudo-first order conditions in acidic aqueous solutions. The dissociation was monitored by following the changes in the visible absorption band of the complex at 25° C. in 5 M HClO$_4$, or at 20, 25, 37, 60, and 90° C. in 5 M HCl. The half-life values determined are collected in Table 5 together with literature values for related compounds: te1pa, cb-te2a and cb-do2a.

TABLE 4

Acid-assisted dissociation inertness for the copper(II) complexes of Hcb-te1pa and of selected literature ligands.

| ligand | conditions | half-life ($t_{1/2}$), min |
|---|---|---|
| | 5M HCl, 90° C. | 0.7 min |
| | 5M HCl, 60° C. | 10.4 min |
| | 5M HCl, 37° C. | 111 min |
| | 5M HCl, 25° C. | 465 min |
| | 5M HCl, 20° C. | 946 min |
| Hcb-te1pa | 5M HClO$_4$, 25° C. | >96 days |
| Hte1pa | 1M HCl, 25° C. | 32 min |
| | 5M HClO$_4$, 25° C. | 144 min |
| H$_2$cb-te2a | 5M HCl, 90° C. | 9240 min |
| H$_2$cb-do2a | 5M HCl, 30° C. | <2 min |

A significant difference between the half-live values in HClO$_4$ and HCl media, especially at 25° C., has been generally explained by the important role that anions sometimes play in the dissociation mechanism.

But more important are the overall very good half-life values obtained for the copper(II) complex of Hcb-te1pa. The experimental kinetic data was used to determine the temperature dependence of the observed rate constants from fitting to the Arrhenius equation. Although an important decrease of the kinetic inertness was found for higher temperatures, the complex half-life is still nearly 2 hours at 37° C. and 5 M HCl.

IV.B.4. Electrochemistry of the Copper(II) Complex

This part corresponds to point e) of the specifications mentioned above.

One of the explanations for the dissociation of copper(II) complexes of macrocyclic ligands in biological media is the metal reduction to copper(I) followed by the demetallation of the complex. It is thus important to ensure the electrochemical inertness as well as the reversibility of the redox system. To determine the redox behavior of the copper complex of Hcb-te1pa, cyclic voltammetry experiments were performed in aqueous solution at pH values of 2.3 and 6.8. The experiments were carried out with a glassy-carbon working electrode in solutions containing 0.1 M NaClO$_4$ as supporting electrolyte.

At neutral pH, a quasi-reversible system at $E_{1/2}$=−0.86 $V_{SCE}$ ($\Delta E_p$=160 mV) was observed with a negligible oxidation peak of free Cu$^+$ ions to Cu$^{2+}$ at 0 $V_{SCE}$. This study indicates that the complex is stable on the CV time scale. Furthermore, the reduction process observed for the copper (II) complex of Hcb-te1pa ($E_{pc}$=−0.696 V versus NHE, upon conversion) is well below the estimated −0.400 V (NHE) threshold for typical bioreductants.

IV.C. Properties Overview and Comparative Data

Specifications for an optimized chelate intended to be used in nuclear medicine are recalled with associated parameters:

| | Specifications | Related parameters |
|---|---|---|
| a | metallation kinetics | time required for complete (>99%) complex formation |
| b | thermodynamic stability | association constant metal-ligand: $K_{MLHh}$ (log $K_{MLHh}$) and calculated pM |
| c | inertness with respect to other metals | association constant with other metals (log $K_{MLHh}'$ and pM') to be compared with log $K_{MLHh}$ and pM |
| d | kinetic inertness | half-life ($t_{1/2}$) (acid-assisted dissociation assay) |
| e | stability upon reduction | cyclic voltammetry assays results |

Values for the copper(II) complex of cb-te1pa are summarized in the table below. Data are compared with those of copper chelates formed with ligands of the prior art.

Especially, properties of copper chelates of cb-te1pa are compared with those of te1pa. The copper chelate of te1pa gives good results relative to the requirements a)-c) of the specifications. However, inertness in acidic medium, (point d) of the specifications, and inertness with regard to reduction (point e) are not optimized, contrary to copper chelate of cb-te1pa.

Data relative to dota and cb-do2a are also provided, as well as for teta and cb-te2a. Introducing a cross-bridge in dota and teta drastically slowers the metallation kinetics, which was surprisingly not observed when cross-bridging te1pa to afford cb-te1pa.

Thermodynamic stability of dota and teta is much lower than that of te1pa and cb-te1pa. Cross-bridging of teta to afford cb-te2a improves thermodynamic stability.

Kinetic inertness in HClO$_4$, 5M at 25° C. is drastically improved for copper chelate of cb-te1pa compared to other chelates.

Moreover, copper chelate of cb-te1pa is the only chelate displaying suitable stability to reduction among those compared in the table below.

Therefore, cb-te1pa provides chelates meeting all requirements of the specifications for an optimized chelate intended to be used in nuclear medicine, which was never achieved with chelates from ligands of the prior art.

| | a) metallation kinetics | b) thermodynamic | | c) inertness | | d) kinetic inertness | | | | e) stability upon reduction Stability Cu(II) -> Cu (I) | |
|---|---|---|---|---|---|---|---|---|---|---|---|
| | time required for | stability | | vs Zn | | half-life (t$_{1/2}$) | | | | | reduction |
| | complete (>99%) Cu complexation | log K$_{[CuL]}$ | pCu | log K$_{[ZnL]}$ | pZn | HClO$_4$, 5M, 25° C. | HCl, 5M, 30° C. | HCl, 5M, 90° C. | reversibility | | potential (V) |
| te1pa | 3 min | 25.50 | 18.64 | 18.86 | 12.00 | 144 min | \ | \ | quasi-reversible | | −1.05 |
| cb-te1pa | 3 min | 26.00 | 15.67 | 18.83 | 8.50 | 96 days | \ | 0.7 min | reversible | | −0.696 |
| dota | fast | 22.21 | 15.19 | 21.01*** | 15.01 | about 5 min | \ | <1 min | irreversible | | −0.74 |
| cb-do2a | too slow | \ | \ | \ | \ | \ | <2 min | <3 min | irreversible | | −0.72 |
| teta | fast | 21.60 | 15.19 | 15.81** | 10.08 | about 8 min | 3.5 days | 4.5 min | irreversible | | −0.98 |
| cb-te2a | too slow | 27.10* | \ | \ | \ | \ | \ | 154 hours | quasi-reversible | | −0.88 |

*estimation by C. Anderson and Ferdani, *Cancer Biother. Radiopharm.*, 2009, 24(4), 379-393
**Delgado and Da Silva, *Talanta*, 1982, 29, 815-822
***Chaves et al., *Talanta*, 1992, 39(3), 249-254

V. Biological Studies

V.I. In Vitro Serum Stability of $^{64}$Cu-Ib-2

In vitro serum stability of $^{64}$Cu-Ib-2 (cf part III.3 above) can be carried out by adding 50 µL of $^{64}$Cu-Ib-2 (1-2 mCi) to 500 µL of FBS (Fetal Bovine Serum). The solution is then incubated at 37° C., and samples is analyzed by radio-TLC at 0, 10, 30, 60 min, and 2, 4, 10, 24, 48, and 72 h postadministration to FBS.

V.2. In Vivo Tests of $^{64}$Cu-Ib-1-Trastuzumab

Animal Models

Xenograft tumor models of NIH3T6.7 cell lines can be prepared using 6-week-old BALB/c nu/nu female nude mice. 5×106 NIH3T6.7 cells were inoculated subcutaneously into left shoulder and right flank of mice. Tumors of appropriate size usually grew within 15 d after the implantation.

Biodistribution

The NIH3T6.7 tumor-bearing BALB/c nude mice (n=4) are injected via tail-vein with $^{64}$Cu-Ib-1-trastuzumab (ca. 20 µCi in 200 µL saline per mouse). Animals are sacrificed at 1 and 2 days postinjection. Organs and tissues of interest (blood, muscle, bone, spleen, kidney, intestine, liver, and tumor) are then removed, weighed, and counted using gamma-counter. The percent of injected dose per gram (% ID/g) can be calculated by comparison to a weighted, counted standard.

MicroPET Imaging in NIH3T6.7 Tumor Bearing Nude Mice

Small animal PET scans and image analysis can be performed using a microPET R4 rodent model scanner. Imaging studies is carried out on female nude mice bearing NIH3T6.7 tumors. The mice are injected via the tail vein with $^{64}$Cu-TE2A-Bn-NCS-trastuzumab (200 µCi). At 1, 2, and 3 days after injection, the mice are anesthetized with 1% to 2% isoflurane, positioned in prone position, and imaged. The images can be reconstructed by a two-dimensional ordered-subsets expectation maximum (OSEM) algorithm.

The invention claimed is:

1. A chelate resulting from the complexation of a ligand of formula (I)

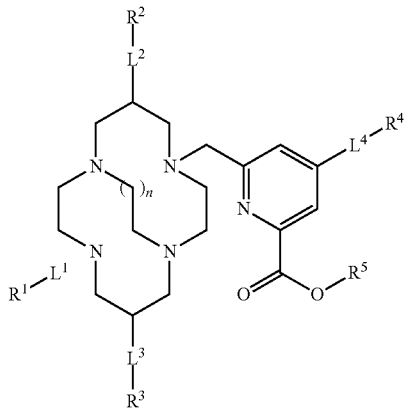

wherein
n is an integer selected from 1 and 2;
R$^1$ represents:
  a hydrogen atom;
  a picolinate arm of formula (II)

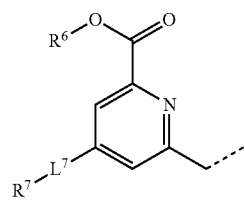

a coupling function, wherein the coupling function is selected from the group consisting of amine; isothiocyanate; isocyanate; activated ester carboxylic acid; activated carboxylic acid; alcohol; alkyne; halide; azide; siloxy; phosphonic acid; thiol; tetrazine; norbornen; oxoamine; aminooxy; thioether;

haloacetamide; glutamate; glutaric anhydride, succinic anhydride, maleic anhydride; aldehyde; ketone; hydrazide; chloroformate and maleimide; or
a vectorizing group, wherein the vectorizing group is selected from the group consisting of antibody; hapten; peptide; protein; sugar; nanoparticle; liposome; lipid; and polyamine;

$R^2$, $R^3$, $R^4$ and $R^7$ each independently represent:
a hydrogen atom;
a coupling function, wherein the coupling function is selected from the group consisting of amine; isothiocyanate; isocyanate; activated ester; carboxylic acid; activated carboxylic acid; alcohol; alkyne; halide; azide; siloxy; phosphonic acid; thiol; tetrazine; norbornen; oxoamine; aminooxy; thioether; haloacetamide; glutamate; glutaric anhydride, succinic anhydride, maleic anhydride; aldehyde; ketone; hydrazide; chloroformate and maleimide; or
a vectorizing group, wherein the vectorizing group is selected from the group consisting of antibody; hapten; peptide; protein; sugar; nanoparticle; liposome; lipid; and polyamine;

$R^5$ and $R^6$ each independently represent:
a hydrogen atom;
an activating function, wherein the activating function is selected from the group consisting of N-hydroxysuccinimide, N-hydroxyglutarimide, maleimide; halide; and —$OCOR^8$ wherein $R^8$ is selected from alkyl and aryl; or
a vectorizing group, wherein the vectorizing group is selected from the group consisting of antibody; hapten; peptide; protein; sugar; nanoparticle; liposome; lipid; and polyamine;

$L^1$, $L^2$, $L^3$, $L^4$ and $L^7$ each independently represent:
a bond; or
a linker selected from the group consisting of alkyl, aryl, arylalkyl, alkylaryl, heteroaryl, heteroarylalkyl, alkylheteroaryl, alkenyl, and alkynyl, wherein alkyl moieties are optionally interrupted by one or more heteroatoms selected from O, N and S;

with a metallic cation selected from the group consisting of copper (II), copper (I), gallium (III), zirconium (IV), technetium (III), indium (III), rhenium (VI), astatine (III), bismuth (III), lead (II), actinium (III), yttrium (III), lutetium (III), samarium (III), terbium (III) and holmium (III).

2. The chelate according to claim 1, wherein the ligand is of formula (Ia') or (Ia")

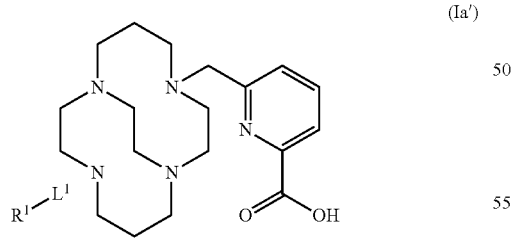

(Ia')

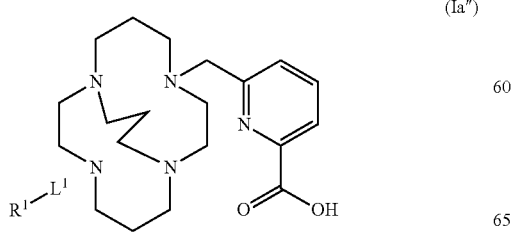

(Ia")

wherein -$L^1$-$R^1$ is selected from formulae (i), (ii), (iii), (iv) and (v):

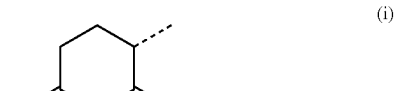

(i)

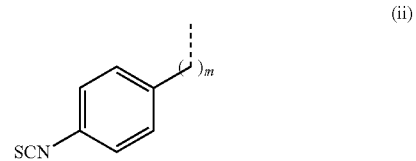

(ii)

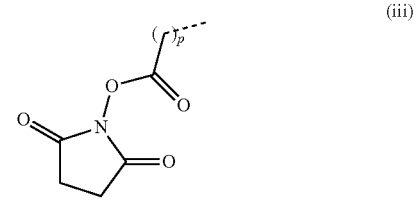

(iii)

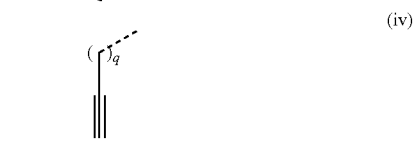

(iv)

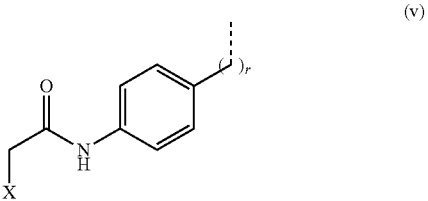

(v)

where in m, p, q and r represent each independently an integer ranging from 0 to 10 and X represents an halogen.

3. The chelate according to claim 1, wherein the ligand is selected from
6-((11-(4-isothiocyanatophenethyl)-1,4,8,11-tetraazabicyclo[6.6.2]hexadecan-4-yl)methyl)picolinic acid;
6-((11-(4-isothiocyanatophenethyl)-1,4,8,11-tetraazabicyclo[6.6.3]heptadecan-4-yl)methyl)picolinic acid;
methyl 6-((6-(4-aminobenzyl)-1,4,8,11-tetraazabicyclo[6.6.2]hexadecan-4-yl)methyl)picolinate;
6-((6-(4-isothiocyanatobenzyl)-1,4,8,11-tetraazabicyclo[6.6.2]hexadecan-4-yl)methyl)picolinic acid;
6-((6-(4-aminobenzyl)-1,4,8,11-tetraazabicyclo[6.6.2]hexadecan-4-yl)methyl)picolinic acid;
6-((6-(2-hydroxyethyl)-1,4,8,11-tetraazabicyclo[6.6.2]hexadecan-4-yl)methyl)picolinic acid;
methyl 6-((13-(4-aminobenzyl)-1,4,8,11-tetraazabicyclo[6.6.2]hexadecan-4-yl)methyl)picolinate;
6-((13-(4-isothiocyanatobenzyl)-1,4,8,11-tetraazabicyclo[6.6.2]hexadecan-4-yl)methyl)picolinic acid;
6-((13-(4-aminobenzyl)-1,4,8,11-tetraazabicyclo[6.6.2]hexadecan-4-yl)methyl)picolinic acid;
6-((13-(2-hydroxyethyl)-1,4,8,11-tetraazabicyclo[6.6.2]hexadecan-4-yl)methyl)picolinic acid;
6-(1,4,8,11-tetraazabicyclo[6.6.2]hexadecan-4-ylmethyl)picolinic acid;
6-(1,4,8,11-tetraazabicyclo[6.6.3]heptadecan-4-ylmethyl)picolinic acid;
6,6'-(1,4,8,11-tetraazabicyclo[6.6.2]hexadecane-4,11-diylbis(methylene))dipicolinic acid; and 6,6'-(1,4,8,11-tetraazabicyclo[6.6.3]heptadecane-4,11-diylbis(methylene))dipicolinic acid.

4. The chelate according to claim 1, wherein the metallic cation is a radioisotope.

5. A pharmaceutical composition comprising the chelate according to claim 1, in association with at least one pharmaceutically acceptable excipient.

6. A ligand of formula (I)

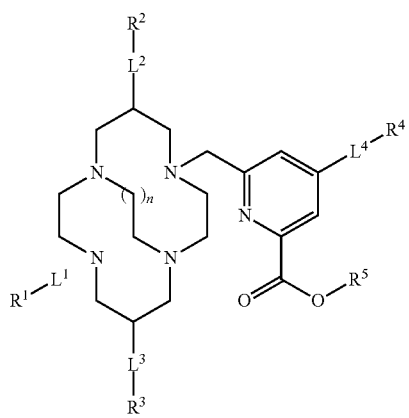

wherein n is an integer selected from 1 and 2;
$R^1$ represents:
  a hydrogen atom;
  a picolinate arm of formula (II)

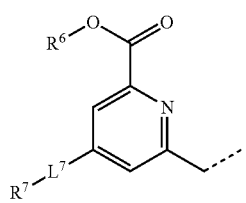

a coupling function, wherein the coupling function is selected from the group consisting of amine; isothiocyanate; isocyanate; activated ester; carboxylic acid; activated carboxylic acid; alcohol; alkyne; halide; azide; siloxy; phosphonic acid; thiol; tetrazine; norbornen; oxoamine; aminooxy; thioether; haloacetamide; glutamate; glutaric anhydride, succinic anhydride, maleic anhydride; aldehyde; ketone; hydrazide; chloroformate and maleimide; or
  a vectorizing group, wherein the vectorizing group is selected from the group consisting of antibody; hapten; peptide; protein; sugar; nanoparticle; liposome; lipid; and polyamine;
$R^2$, $R^3$, $R^4$ and $R^7$ each independently represent:
  a hydrogen atom;
  a coupling function, wherein the coupling function is selected from the group consisting of amine; isothiocyanate; isocyanate; activated ester; carboxylic acid; activated carboxylic acid; alcohol; alkyne; halide; azide; siloxy; phosphonic acid; thiol; tetrazine; norbornen; oxoamine; aminooxy; thioether; haloacetamide; glutamate; glutaric anhydride, succinic anhydride, maleic anhydride; aldehyde; ketone; hydrazide; chloroformate and maleimide; or
  a vectorizing group, wherein the vectorizing group is selected from the group consisting of antibody; hapten; peptide; protein; sugar; nanoparticle; liposome; lipid; and polyamine;
$R^5$ and $R^6$ each independently represent:
  a hydrogen atom;
  an activating function, wherein the activating function is selected from the group consisting of N-hydroxysuccinimide, N-hydroxyglutarimide, maleimide; halide; and —$OCOR^8$ wherein $R^8$ is selected from alkyl and aryl; or
  a vectorizing group, wherein the vectorizing group is selected from the group consisting of antibody; hapten; peptide; protein; sugar; nanoparticle; liposome; lipid; and polyamine;
$L^1$, $L^2$, $L^3$, $L^4$ and $L^7$ each independently represent:
  a bond; or
  a linker selected from the group consisting of alkyl, aryl, arylalkyl, alkylaryl, heteroaryl, heteroarylalkyl, alkylheteroaryl, alkenyl and alkynyl, wherein alkyl moieties are optionally interrupted by one or more heteroatoms selected from O, N and S.

7. The ligand according to claim 6, wherein at least one of -$L^1$-$R^1$, -$L^2$-$R^2$, -$L^3$-$R^3$ and -$L^4$-$R^4$ is selected from formulae (i), (ii), (iii), (iv), (v), (vi) and (vii):

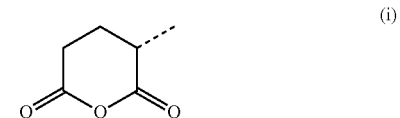

(i)

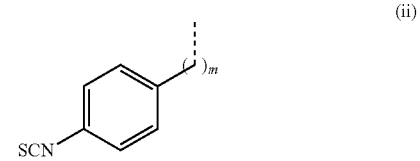

(ii)

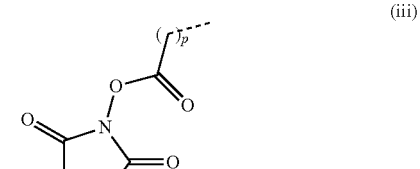

(iii)

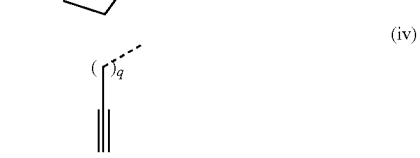

(iv)

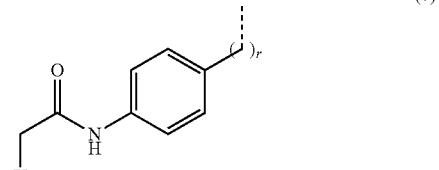

(v)

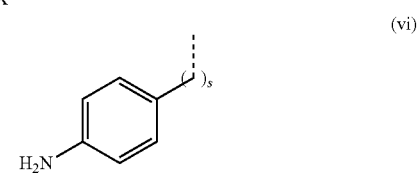

(vi)

(vii)

wherein m, p, q, r, s and t represent each independently an integer ranging from 0 to 10 and X represents an halogen.

8. The ligand according to claim 6, of formula (Ia') or (Ia")

(Ia')

(Ia")

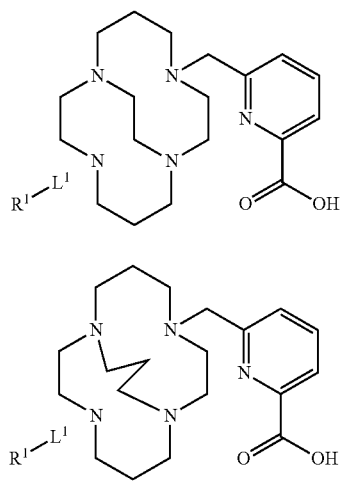

wherein R¹ and L¹ are as previously defined.

9. The ligand according to claim 6, of formula (Ib-R⁵), (Ic-R⁵), (Ib) or (Ic)

(Ib-R⁵)

(Ic-R⁵)

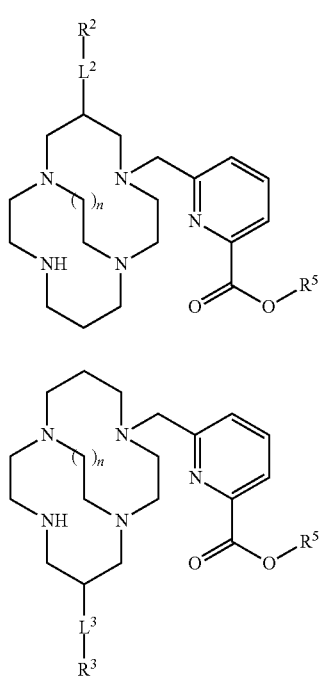

(Ib)

(Ic)

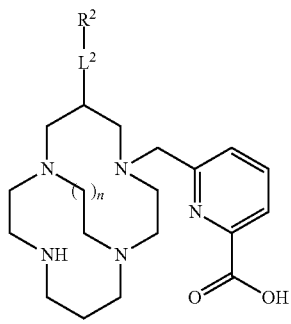

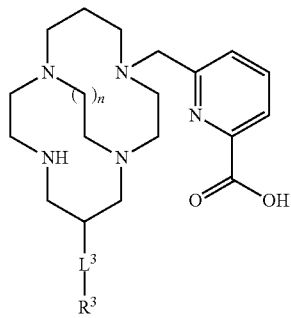

wherein R², R³, L² and L³ are as previously defined, and n is an integer selected from 1 or 2.

10. The ligand according to claim 6, selected from:
- 6-((11-(4-isothiocyanatophenethyl)-1,4,8,11-tetraazabicyclo[6.6.2]hexadecan-4-yl)methyl)picolinic acid;
- 6-((11-(4-isothiocyanatophenethyl)-1,4,8,11-tetraazabicyclo[6.6.3]heptadecan-4-yl)methyl)picolinic acid;
- methyl 6-((6-(4-aminobenzyl)-1,4,8,11-tetraazabicyclo[6.6.2]hexadecan-4-yl)methyl)picolinate;
- 6-((6-(4-isothiocyanatobenzyl)-1,4,8,11-tetraazabicyclo[6.6.2]hexadecan-4-yl)methyl)picolinic acid;
- 6-((6-(4-aminobenzyl)-1,4,8,11-tetraazabicyclo[6.6.2]hexadecan-4-yl)methyl)picolinic acid;
- 6-((6-(2-hydroxyethyl)-1,4,8,11-tetraazabicyclo[6.6.2]hexadecan-4-yl)methyl)picolinic acid;
- methyl 6-((13-(4-aminobenzyl)-1,4,8,11-tetraazabicyclo[6.6.2]hexadecan-4-yl)methyl)picolinate;
- 6-((13-(4-isothiocyanatobenzyl)-1,4,8,11-tetraazabicyclo[6.6.2]hexadecan-4-yl)methyl)picolinic acid;
- 6-((13-(4-aminobenzyl)-1,4,8,11-tetraazabicyclo[6.6.2]hexadecan-4-yl)methyl)picolinic acid;
- 6-((13-(2-hydroxyethyl)-1,4,8,11-tetraazabicyclo[6.6.2]hexadecan-4-yl)methyl)picolinic acid;
- 6-(1,4,8,11-tetraazabicyclo[6.6.2]hexadecan-4-ylmethyl)picolinic acid;
- 6-(1,4,8,11-tetraazabicyclo[6.6.3]heptadecan-4-ylmethyl)picolinic acid;
- 6,6'-(1,4,8,11-tetraazabicyclo[6.6.2]hexadecane-4,11-diylbis(methylene))dipicolinic acid; and
- 6,6'-(1,4,8,11-tetraazabicyclo[6.6.3]heptadecane-4,11-diylbis(methylene))dipicolinic acid.

11. A process for manufacturing a ligand according to claim 6, comprising:
reacting compound of formula (i)

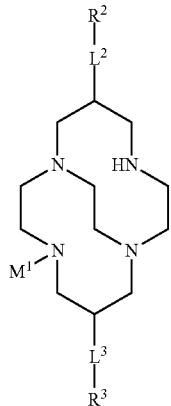

wherein
$L^2, R^2, L^3$ and $R^3$ are as defined in formula (I) as previously defined; and
$M_1$ represents:
a hydrogen atom,
an amino-protecting group, or
$-L^1-R^1$, wherein $L^1$ and $R^1$ are as defined in formula (I) as previously defined;
with compound of formula (ii)

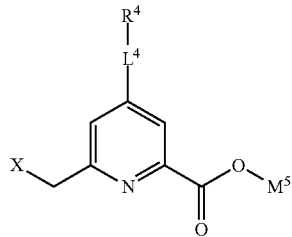

wherein
$L^4$ and $R^4$ are as defined in formula (I) as previously defined,
X represents an halogen atom; and
$M^5$ represents
a protecting group selected from alkyl group, or $R^5$, wherein $R^5$ are as defined in formula (I) as previously defined, provided that it does not represents a hydrogen atom;

to afford compound of formula (iii)

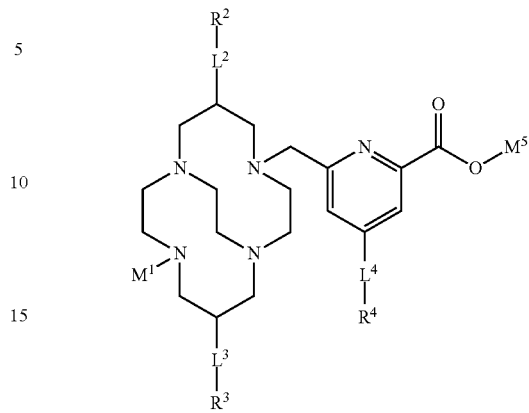

wherein $L^2$, $R^2$, $L^3$, $R^3$, $L^4$ and $R^4$ are as defined in formula (I) as previously defined and $M^1$ and $M^5$ are as defined above;
and where needed conducting on (iii) one or more subsequent step selected from:
deprotecting the acidic function protected by $M^5$, to afford compound of formula (I) as previously defined, wherein $R^5$ represents a hydrogen atom;
introducing an activating function or a vectorizing group on the acidic function to afford compound of formula (I) as previously, wherein $R^5$ represents an activating function or a vectorizing group;
deprotecting the amine function protected by $M^1$, to afford compound of formula (I) as previously defined, wherein $-L^1-R^1$ represents —H; and
introducing $-L^1-R^1$ on the amine function, wherein $L^1-R^1$ is as defined in in formula (I) as previously defined;
to afford compound of formula (I).

12. The chelate according to claim 1, wherein the metallic cation is a radioisotope selected from the group consisting of $^{64}$Cu(II), $^{67}$Cu(II), $^{68}$Ga(III), $^{89}$Zr(IV), $^{99m}$Tc(III), $^{111}$In(III), $^{186}$Re(VI), $^{188}$Re(VI), $^{210}$At(III), $^{212}$Bi ($^{212}$Pb), $^{213}$Bi(III), $^{225}$Ac(III), $^{90}$Y(III), $^{177}$Lu(III), $^{153}$Sm(III), $^{149}$Tb(III) and $^{166}$Ho(III).

13. The process according to claim 11, wherein in compound of formula (i) M represents an amino-protecting group selected from a carbobenzyloxy, a p-methoxybenzyl carbonyl, a tert-butoxy carbonyl, a 9-fluorenylmethyloxycarbonyl, a benzoyl, a benzyl, a carbamate group, a p-methoxybenzyl, a 3,4-dimethoxybenzyl, a p-methoxyphenyl, a tosyl and an arylsulphonyl.

* * * * *